(12) United States Patent
Fadli

(10) Patent No.: US 9,345,653 B2
(45) Date of Patent: May 24, 2016

(54) DYE COMPOSITION COMPRISING A CATIONIC META-PHENYLENEDIAMINE

(71) Applicant: Aziz Fadli, Chelles (FR)

(72) Inventor: Aziz Fadli, Chelles (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/411,841

(22) PCT Filed: Jun. 26, 2013

(86) PCT No.: PCT/EP2013/063389
§ 371 (c)(1),
(2) Date: Dec. 29, 2014

(87) PCT Pub. No.: WO2014/005900
PCT Pub. Date: Jan. 9, 2014

(65) Prior Publication Data
US 2015/0143638 A1 May 28, 2015

Related U.S. Application Data

(60) Provisional application No. 61/695,316, filed on Aug. 31, 2012.

(30) Foreign Application Priority Data

Jul. 2, 2012 (FR) ..................... 12 56309

(51) Int. Cl.
*A61Q 5/10* (2006.01)
*A61K 8/49* (2006.01)
*C07D 233/61* (2006.01)
*C07D 295/037* (2006.01)

(52) U.S. Cl.
CPC . *A61K 8/494* (2013.01); *A61Q 5/10* (2013.01); *C07D 233/61* (2013.01); *C07D 295/037* (2013.01)

(58) Field of Classification Search
CPC ......... A61Q 5/10; A61K 8/494; A61K 8/416; A61K 8/4946
USPC ..................................... 8/411, 405
See application file for complete search history.

(56) References Cited

U.S. PATENT DOCUMENTS

| | | | |
|---|---|---|---|
| 4,003,699 A | 1/1977 | Rose et al. | |
| 4,125,367 A | 11/1978 | Bugaut et al. | |
| RE30,199 E | 1/1980 | Rose et al. | |
| 4,259,261 A | 3/1981 | Bugaut et al. | |
| 4,329,504 A | 5/1982 | Bugaut et al. | |
| 4,823,985 A | 4/1989 | Grollier et al. | |
| 4,842,612 A | 6/1989 | Rose et al. | |
| 5,061,289 A | 10/1991 | Clausen et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,766,576 A | 6/1998 | Lowe et al. | |
| 6,099,592 A | 8/2000 | Vidal et al. | |
| 6,099,593 A | 8/2000 | Terranova et al. | |
| 6,248,137 B1 | 6/2001 | Terranova et al. | |
| 6,284,003 B1 | 9/2001 | Rose et al. | |
| 6,338,741 B1 | 1/2002 | Vidal et al. | |
| 6,544,298 B1 | 4/2003 | Vidal et al. | |
| 6,645,258 B2 | 11/2003 | Vidal et al. | |
| 6,730,789 B1 | 5/2004 | Birault et al. | |
| 6,783,557 B1 | 8/2004 | Terranova et al. | |
| 2001/0005914 A1* | 7/2001 | Bittner et al. | ..... 8/405 |
| 2001/0020310 A1 | 9/2001 | Terranova et al. | |
| 2002/0050013 A1 | 5/2002 | Vidal et al. | |
| 2003/0019051 A9 | 1/2003 | Vidal et al. | |
| 2005/0166335 A1 | 8/2005 | Vidal et al. | |
| 2007/0136959 A1 | 6/2007 | Fadli | |
| 2007/0143935 A1 | 6/2007 | Fadli et al. | |
| 2008/0071092 A1 | 3/2008 | Vidal et al. | |
| 2010/0115711 A1 | 5/2010 | Fadli et al. | |

FOREIGN PATENT DOCUMENTS

DE 2359399 A1 6/1975
DE 3843892 A1 6/1990
(Continued)

OTHER PUBLICATIONS

STIC Search Report dated Mar. 20, 2015.*
L. Spiegel et al. (Die Reduction des O.P-Dinitrophenyl-piperidins pp. 2631-2638 (1933).*
Chem. Ber 102, pp. 1529-1533 (1969).*
International Search Report and Written Opinion for PCT/EP2013/063389 (Aug. 27, 2013).
English language abstract for EP 0770375 (May 2, 1997).
English language abstract for JP 02-019576 (Jan. 23, 1990).
English language abstract for JP 05-163124 (Jun. 29, 1993).

*Primary Examiner* — Eisa Elhilo
(74) *Attorney, Agent, or Firm* — The Marbury Law Group, PLLC

(57) ABSTRACT

One subject of the invention is a meia-phenylenediamine compound having formula (I) below, the addition salts thereof with an acid and the solvates thereof: in which: • R represents a hydrogen or halogen atom; a $C_1$-$C_4$ alkyl group; a carboxyl group or a ($C_1$-$C_4$)alkoxycarbonyl group, • R1 represents a $C_1$-$C_{10}$(hydroxy)alkyl group, optionally interrupted with one or more non-adjacent oxygen atoms or non-adjacent NR' substituents, substituted by a cationic CAT group, • R2 represents a hydrogen atom or a $C_1$-$C_4$(hydroxy)alkyl group, • R1 and R2 may form, together with the atom that bears them, a cationic heterocycle with 5 to 8 members, • R' represents a hydrogen atom or a $C_1$-$C_4$(hydroxy)alkyl group; • An" represents an anion or a mixture of anions which are organic or inorganic and cosmetically acceptable.

(I)

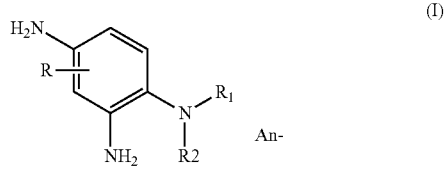

18 Claims, No Drawings

(56) References Cited

FOREIGN PATENT DOCUMENTS

| | | | |
|---|---|---|---|
| DE | 4133957 | A1 | 4/1993 |
| DE | 19543988 | A1 | 5/1997 |
| EP | 0286896 | A2 | 10/1988 |
| EP | 0770375 | A1 | 5/1997 |
| EP | 0926149 | A1 | 6/1999 |
| EP | 1792606 | A1 | 6/2007 |
| EP | 1792903 | A1 | 6/2007 |
| FR | 1136996 | * | 5/1957 |
| FR | 2362116 | A1 | 3/1978 |
| FR | 2585913 | A1 | 3/1987 |
| FR | 2733749 | A1 | 11/1996 |
| FR | 2801308 | A1 | 5/2001 |
| FR | 2866338 | A1 | 8/2005 |
| FR | 2927078 | A1 | 8/2009 |
| GB | 303093 | A | 12/1928 |
| GB | 1026978 | A | 4/1966 |
| GB | 1153196 | A | 5/1969 |
| JP | 02-019576 | A | 1/1990 |
| JP | 05-163124 | A | 6/1993 |
| WO | 94/08969 | A1 | 4/1994 |
| WO | 94/08970 | A1 | 4/1994 |
| WO | 96/15765 | A1 | 5/1996 |
| WO | 97/49378 | A1 | 12/1997 |
| WO | 00/42979 | A1 | 7/2000 |
| WO | 00/43396 | A1 | 7/2000 |
| WO | 2009/098257 | A1 | 8/2009 |

* cited by examiner

DYE COMPOSITION COMPRISING A CATIONIC META-PHENYLENEDIAMINE

CROSS REFERENCE TO RELATED APPLICATIONS

This is a national stage application of PCT/EP2013/063389, filed internationally on Jun. 26, 2013, which claims priority to U.S. Provisional Application No. 61/695,316, filed on Aug. 31, 2012, as well as French Application No. 1256309, filed Jul. 2, 2012.

The invention relates to particular novel cationic meta-phenylenediamine compounds, a dye composition comprising the latter and also a dyeing process using these compounds.

It is known practice to dye keratin fibres and in particular human hair with dye compositions containing oxidation dye precursors, which are generally known as oxidation bases, such as ortho- or para-phenylenediamines, ortho- or para-aminophenols and heterocyclic compounds. These oxidation bases are colourless or weakly coloured compounds, which, when combined with oxidizing products, may give rise to coloured compounds via a process of oxidative condensation.

It is also known that the shades obtained with these oxidation bases may be varied by combining them with couplers or colour modifiers, the latter being chosen especially from aromatic meta-diamines, meta-aminophenols, meta-diphenols and certain heterocyclic compounds such as indole compounds.

The variety of molecules used as oxidation bases and couplers allows a wide range of colours to be obtained.

The "permanent" colour obtained by means of these couplers and oxidation dyes must moreover satisfy a certain number of requirements. Thus, it should have no toxicological drawbacks, it should allow shades to be obtained in the desired intensity, and it should show good resistance to external agents such as light, bad weather, washing, permanent waving treatments, perspiration and rubbing.

The dyes should also allow grey hair to be covered and, finally, they should be as unselective as possible, i.e. they should produce the smallest possible differences in colour along a same keratin fibre, which in general is differently sensitized (i.e. damaged) between its tip and its root.

It is already known practice to use couplers of the meta-phenylenediamine type for dyeing keratin fibres, especially the hair. For instance, from document FR 2362116, substituted meta-phenylenediamine couplers are known. These couplers may have the drawbacks of resulting in colours that are not sufficiently intense or chromatic and/or that are too selective.

The aim of the present invention is to obtain a hair dye composition that has improved dyeing properties in terms of intensity or chromaticity and/or selectivity and/or resistance to external agents.

Surprisingly and advantageously, the Applicant has now found a new family of couplers composed of cationic meta-phenylenediamines. These couplers result in a wide range of colours in oxidation dyeing. They make it possible in particular to expand the colour range while improving the harmlessness of the couplers of the oxidation dye. Furthermore, these cationic meta-phenylenediamines make it possible to obtain colours having varied shades and that are powerful and chromatic.

One subject of the invention is therefore a meta-phenylenediamine compound having the following formula (I), the addition salts thereof and the solvates thereof:

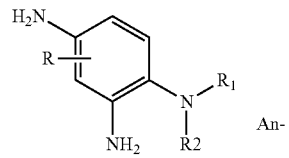

in which:
R represents a hydrogen or halogen atom; a $C_1$-$C_4$ alkyl group; a carboxyl group or a $(C_1$-$C_4)$alkoxycarbonyl group;
R1 represents a $C_1$-$C_{10}$ (hydroxy)alkyl group, optionally interrupted with one or more non-adjacent oxygen atoms or non-adjacent NR' substituents, substituted by a cationic CAT group,
R2 represents a hydrogen atom or a $C_1$-$C_4$(hydroxy)alkyl group,
R1 and R2 may form, together with the atom that bears them, a cationic heterocycle with 5 to 8 members,
R' represents a hydrogen atom or a $C_1$-$C_4$(hydroxy)alkyl group,
An⁻ represents an anion or a mixture of anions which are organic or inorganic and cosmetically acceptable.

Another subject of the invention is a composition for dyeing keratin fibres comprising, in a suitable dyeing medium, at least one meta-phenylenediamine compound having formula (I) as defined above. Another subject of the invention is a process for dyeing keratin fibres consisting in applying this composition to said fibres.

Another subject of the invention is the use of the composition of the present invention for dyeing keratin fibres, in particular human keratin fibres such as the hair.

The invention also relates to multi-compartment devices comprising compositions containing one or more couplers chosen from the compound having formula (I) or an addition salt thereof with an acid.

A final subject of the invention is a dyeing kit comprising, on the one hand, a dye composition containing a compound having formula (I) and, on the other hand, a composition containing an oxidizing agent.

The compounds of the present invention make it possible in particular to obtain compositions for dyeing keratin fibres that are suitable for use in oxidation dyeing and that make it possible to obtain a hair colour that has improved dyeing properties in terms of intensity or chromaticity and/or selectivity and/or resistance to external agents such as shampoo, sweat, permanent reshaping and light.

For the purposes of the present invention, and unless otherwise indicated:
an "alkyl group" is a straight or branched $C_1$-$C_{20}$ and preferably $C_1$-$C_8$ hydrocarbon-based group;
a "(hydroxy)alkyl" is an alkyl group optionally substituted by a at least a hydroxyl group
an "alkenylene group" is an unsaturated hydrocarbon-based divalent group as defined previously, which may contain from 1 to 4 conjugated or unconjugated —C=C— double bonds; the alkenylene group particularly contains 1 or 2 unsaturated groups;
the expression "optionally substituted" attributed to the alkyl group means that said alkyl group may be substituted by one or more groups chosen from the following groups: i) hydroxyl, ii) $C_1$-$C_4$ alkoxy, iii) acylamino, iv) amino optionally substituted by one or two identical or different $C_1$-$C_4$ alkyl groups, said alkyl groups possibly forming with the nitrogen atom that bears them a 5- to 7-membered heterocycle, optionally comprising another heteroatom identical to or different from nitrogen; v) or a quaternary ammonium substituent —N⁺R'R"R'", M⁻ for which R', R" and R'", which may be identical or different, represent a hydrogen atom or a $C_1$-$C_4$ alkyl substituent, or else —N⁺R'R"R'" forms a heteroaryl such as imidazolium optionally substituted by a $C_1$-$C_4$ alkyl substituent, and M⁻ represents the counterion of the corresponding organic acid, inorganic acid or halide;

an "alkoxy group" is an alkyl-oxy group for which the alkyl group is a straight or branched $C_1$-$C_{16}$ and preferentially $C_1$-$C_8$ hydrocarbon-based group;

when the alkoxy substituent is optionally substituted, this implies that the alkyl group is optionally substituted as defined hereinabove;

the expression "at least one" is equivalent to "one or more"; and the term "inclusive" for a range of concentrations means that the limits of that range are included in the defined range.

It should be noted that, in the text hereinbelow, unless otherwise indicated, the limits of a range of values are included in that range.

Compound Having Formula (I)

One subject of the invention is therefore a meta-phenylenediamine compound having the following formula (I), the addition salts thereof and the solvates thereof:

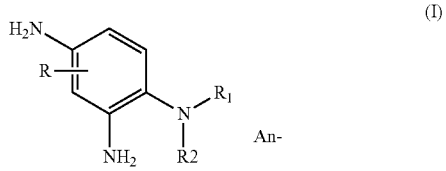

where:
R represents a hydrogen or halogen atom; a $C_1$-$C_4$ alkyl group; a carboxyl group or a ($C_1$-$C_4$) alkoxycarbonyl group,
R1 represents a $C_1$-$C_{10}$ (hydroxy)alkyl group, optionally interrupted with one or more non-adjacent oxygen atoms or non-adjacent NR' substituents, substituted by a cationic CAT group,
R2 represents a hydrogen atom or a $C_1$-$C_4$(hydroxy)alkyl group,
R1 and R2 may form, together with the atom that bears them, a cationic heterocycle with 5 to 8 members,
R' represents a hydrogen atom or a $C_1$-$C_4$(hydroxy)alkyl group;
An⁻ represents an anion or a mixture of anions which are organic or inorganic and cosmetically acceptable.

The electroneutrality of the compounds having formula (I) is ensured by an anion or a mixture of anions, labelled An⁻, which are organic or inorganic and are cosmetically acceptable.

An⁻ represents an anion or a mixture of anions chosen, for instance, from a halide such as chloride, bromide, fluoride or iodide; a hydroxide; a sulfate; a hydrogen sulfate; an alkylsulfate in which the straight or branched alkyl part is $C_1$-$C_6$, such as the methylsulfate or ethylsulfate ion; carbonates and hydrogen carbonates; salts of carboxylic acids, such as formate, acetate, citrate, tartrate and oxalate; alkyl sulfonates for which the straight or branched alkyl part is $C_1$-$C_6$, such as the methylsulfonate ion; arylsulfonates for which the aryl part, preferably phenyl, is optionally substituted by one or more $C_1$-$C_4$ alkyl groups, for instance 4-toluylsulfonate; and alkylsulfonyls such as mesylate.

The compounds having general formula (I) may be in free form or in the form of salts, such as addition salts with an inorganic acid preferably chosen from hydrochloric acid, hydrobromic acid, sulfuric acid sulfates, phosphoric acid or with an organic acid such as, for instance, citric acid, succinic acid, tartaric acid, lactic acid, 4-toluylsulfonic acid, benzenesulfonic acid, acetic acid, para-toluenesulfonic acid, formic acid and methanesulfonic acid.

The compounds having general formula (I) may also be in the form of solvates, for instance a hydrate or a solvate of a straight or branched alcohol such as ethanol or isopropanol.

In the context of the invention, a derivative having formula (I) is understood to encompass all mesomeric or isomeric forms.

In the context of the invention, the expression "cationic CAT group present in the compound having formula (I)" is understood to mean any straight or branched or heterocyclic group comprising a quaternary ammonium, this quaternary ammonium being of the type —N⁺RaRbRc, Ra, Rb and Rc, which may be identical or different, representing a $C_1$-$C_6$ alkyl group which may be substituted by a hydroxyl. Ra and Rb may together form a 5- to 10-membered, preferably a 5- to 8-membered heterocycle, in which case the group Rc is a $C_1$-$C_6$ alkyl group which may be substituted by a hydroxyl group or a $C_1$-$C_4$ (hydroxy)alkyl group.

Preferably, Ra, Rb, Rc, identical or different, represent a $C_1$-$C_2$ alkyl group, in particular methyl, ethyl, optionally substituted by a hydroxyl group.

Preferably, when Ra and Rb together form a 5- to 8-membered heterocycle comprising a 5- to 8-membered heterocycle, group Rc is a $C_1$-$C_2$ alkyl group which may be substituted by a hydroxyl group or a $C_1$-$C_4$ (hydroxy)alkyl group.

Accordingly, compounds having formula (I) according to the invention bear a permanent cationic charge that is independent of the pH of the medium in which the compounds are formulated.

As examples of cationic groups, mention may be made of trimethylammonium, triethylammonium, dimethylethylammonium, diethylmethylammonium, diisopropylmethylammonium, diethylpropylammonium, hydroxyethyldiethylammonium, di-beta-hydroxyethylmethylammonium, di-beta-hydroxyethylammonium, tri-beta-hydroxyethylammonium, and mixtures thereof.

Cationic heterocycle is understood to mean a 5- to 10-membered, preferably 5 to 8-membered heterocycle, chosen from condensed or not condensed heterocycle, of which one of the members is a quaternary ammonium or a non-cationic heterocyclic group substituted by a cationic group —N⁺RaRbRc, Ra, Rb, Rc identical or different representing a $C_1$-$C_6$ alkyl group that may be substituted by a hydroxyl and preferably chosen from trimethylammonium, triethylammonium, dimethyl-ethyl ammonium, diethylmethylammonium, diisopropylmethylammonium, diethyl-propyl ammonium, hydroxyethyl diethyl ammonium, di-beta-hydroxyethylmethylammonium, di-beta-hydroxyethylethylammonium, tri-beta-hydroxyethylammonium groups, and mixtures thereof.

As examples of cationic heterocycles, mention may be made of imidazolium, pyridinium, piperidinium, piperazinium, pyrrolidinium, morpholinium, pyrimidinium, thiazolium, benzimidazolium, benzothiazolium, oxazolium, benzotriazolium, pyrazolium, triazolium, benzoxazolium groups, these cationic heterocycles being optionally substituted by one or more groups, identical or different, chosen from a hydroxyl group or a $C_1$-$C_4$ (hydroxy)alkyl group, and mixtures thereof.

As examples of cationic heterocycles mention may also be made of pyrrolidine or piperidine or piperazine groups, substituted by a cationic —N⁺RaRbRc group, Ra, Rb, Rc identical or different, representing a $C_1$-$C_6$ alkyl group that can be substituted by a hydroxyl and preferably chosen from trimethylammonium, triethylammonium, dimethylethyl ammonium, diethylmethylammonium, diisopropylmethylammonium, diethyl-propyl ammonium, hydroxyethyl diethyl ammonium, di-beta-hydroxyethylmethylammonium, tri-beta-hydroxyethylammonium and in particular the pyrrolidine group or piperidine group, substituted by a tri($C_1$-$C_4$) alkyl ammonium group, and mixtures thereof.

Preferably, cationic groups are chosen from trimethylammonium, triethylammonium, di-beta-hydroxyethylmethylammonium, tri-beta-hydroxyethylammonium groups; imidazolium, pyridinium, piperidinium, piperazinium, pyrrolidinium, morpholinium groups, these cationic heterocycles being optionally substituted by one or more groups identical or different chosen from a hydroxyl group or a $C_1$-$C_4$ (hydroxy)alkyl group; pyrrolidine or piperidine groups substituted by a tri($C_1$-$C_4$)alkyl ammonium group, and mixtures thereof.

According to one preferred embodiment, in formula (I):
R represents a hydrogen atom,
R1 represents a $C_1$-$C_{10}$(hydroxy)alkyl group, optionally interrupted with an oxygen atom or with an NR' substituent, substituted by a cationic CAT group,
R2 represents a hydrogen atom or a $C_1$-$C_4$(hydroxy)alkyl group,
R1 and R2 may form, together with the atom that bears them, a cationic heterocycle with 5 to 8 members,
R' represents a hydrogen atom or a $C_1$-$C_4$ alkyl group;
An⁻ represents an anion or a mixture of anions which are organic or inorganic and are cosmetically acceptable, Preferably, the cationic group is chosen from trimethylammonium, triethylammonium, dimethylethylammonium, diethylmethylammonium, diisopropylmethylammonium, hydroxyethyldiethylammonium, imidazolium, pyridinium, piperazinium, pyrrolidinium, morpholinium, pyrimidinium, thiazolium, benzimidazolium and piperidinium groups and mixtures thereof.

More preferably still, the cationic groups are chosen from trimethylammonium, imidazolium, piperazinium, pyrrolidinium, piperidinium and morpholinium groups and mixtures thereof.

I/ According to a first embodiment of the invention, the compounds having formula (I) are such that:
R1 represents a $C_1$-$C_{10}$ alkyl group, substituted by a cationic CAT group,
R2 represents a hydrogen atom or a $C_1$-$C_4$ alkyl group,
R' represents a hydrogen atom or a $C_1$-$C_4$ alkyl group, preferably a hydrogen atom or a methyl group and
R represents a hydrogen atom.
Where the cationic CAT group is as defined previously.
a) According to a first variant of this first embodiment, in formula (I), CAT designates a cationic group chosen from trimethylammonium, triethylammonium, dimethyl-ethyl ammonium, diethylmethylammonium, diisopropylmethylammonium, diethyl-propyl ammonium, hydroxyethyl diethyl ammonium, di-beta-hydroxyethylmethylammonium, tri-beta-hydroxyethylammonium groups and mixtures thereof, more preferably a cationic group chosen from trimethylammonium groups.
b) According to a second variant of this first embodiment, in formula (I), CAT designates a 5- to 10-membered, preferably 5 to 8-membered heterocyclic group, that may be condensed or not condensed heterocyclic group, of which one member is a quaternary ammonium, said heterocycle being optionally substituted by one or more groups, identical or different, chosen from a hydroxy group or a $C_1$-$C_4$ (hydroxy)alkyl group.

As examples of such heterocyclic groups, mention may be made of imidazolium, pyridinium, piperidinium, piperazinium, pyrrolidinium, morpholinium, pyrimidinium, thiazolium, benzimidazolium, benzothiazolium, oxazolium, benzotriazolium, pyrazolium, triazolium, benzoxazolium groups, these cationic heterocycles being optionally substituted by one or more groups, identical or different, chosen from a hydroxyl group or a $C_1$-$C_4$ (hydroxy)alkyl group.

According to this preferred form, the heterocycles are preferentially chosen from piperazinium, pyrrolidinium, morpholinium, imidazolium, piperidinium groups, and mixtures thereof, and these heterocycles are optionally substituted by one or more groups identical or different chosen from a hydroxy group or a $C_1$-$C_4$ (hydroxy)alkyl group.

c) According to a third variant of this first embodiment, in formula (I), CAT designates a pyrrolidine or piperidine or piperazine group, substituted by a cationic —N⁺RaRbRc group, Ra, Rb, Rc identical or different, representing a $C_1$-$C_6$ alkyl group that can be substituted by a hydroxy and preferably chosen from trimethylammonium, triethylammonium, dimethylethyl ammonium, diethylmethylammonium, diisopropylmethylammonium, diethylpropyl ammonium, hydroxyethyl diethyl ammonium, di-beta-hydroxyethylmethylammonium, tri-beta-hydroxyethylammonium and in particular the pyrrolidine group or piperidine group, substituted by a tri($C_1$-$C_4$)alkyl ammonium group.

II/ According to a second embodiment of the invention, the compounds having formula (I) are such that:
R1 represents a $C_1$-$C_{10}$ alkyl group interrupted with an oxygen atom or with an NR' substituent, substituted by a cationic CAT group,
R2 represents a hydrogen atom or a $C_1$-$C_4$ alkyl group,
R' represents a hydrogen atom or a $C_1$-$C_4$ alkyl group, preferably a hydrogen atom,
R represents a hydrogen atom.
a) According to a first variant of this second embodiment, in formula (I), CAT designates a cationic group chosen from trimethylammonium, triethylammonium, dimethylethyl ammonium, diethylmethylammonium, diisopropylmethylammonium, diethylpropyl ammonium, hydroxyethyl diethyl ammonium, di-beta-hydroxyethylmethylammonium, di-beta-hydroxyethylethylammonium, tri-beta-hydroxyethylammonium groups, more preferably a cationic trimethylammonium group.
b) According to a second variant of this second embodiment, in formula (I), CAT designates a 5- to 10-membered, preferably 5- to 8-membered heterocyclic group of which one member is a quaternary ammonium, that may be condensed or not condensed heterocyclic group, said heterocycle being optionally substituted by one or more groups, identical or different, chosen from a hydroxy group or a $C_1$-$C_4$ (hydroxy)alkyl group.

As examples of such heterocyclic groups, mention may be made of imidazolium, pyridinium, piperidinium, piperazinium, pyrrolidinium, morpholinium, pyrimidinium, thiazolium, benzimidazolium, benzothiazolium, oxazolium, benzotriazolium, pyrazolium, triazolium, benzoxazolium groups, these cationic heterocycles being optionally substituted by one or more groups, identical or different, chosen from a hydroxyl group or a $C_1$-$C_4$ (hydroxy)alkyl group.

According to this preferred form, the heterocycles are preferentially chosen from piperazinium, pyrrolidinium, morpholinium, imidazolium, piperidinium, and these heterocycles are optionally substituted by one or more groups identical or different chosen from a hydroxy group or a $C_1$-$C_4$ (hydroxy)alkyl group.

c) According to a third variant of this second embodiment, in formula (I), CAT designates a pyrrolidine or piperidine or piperazine group, substituted by a cationic —N⁺RaRbRc group, Ra, Rb, Rc identical or different, representing a $C_1$-$C_6$ alkyl group that can be substituted by a hydroxy and preferably chosen from trimethylammonium, triethylammonium, dimethyl-ethyl ammonium, diethylmethylammonium, diisopropylmethylammonium, diethyl-propyl ammonium, hydroxyethyl diethyl ammonium, di-beta-hydroxyethylmethylammonium, tri-beta-hydroxyethylammonium and in particular the pyrrolidine group or piperidine group, substituted by a tri($C_1$-$C_4$)alkyl ammonium group.

II/ According to a third embodiment of the invention, the compounds having formula (I) are such that:

R1 and R2 form, together with the atom that bears them, a cationic heterocycle with 5 to 8 members.

R' represents a hydrogen atom or a $C_1$-$C_4$ alkyl group, preferably a hydrogen atom.

According to a first preferred form of this variant, R1 and R2 form, together with the nitrogen atom that bears them, a 5- to 8-membered heterocyclic group of which one member is a quaternary ammonium, said heterocycle being optionally substituted by one or more groups, identical or different, chosen from a hydroxy group or a $C_1$-$C_4$ (hydroxy)alkyl group.

According to this preferred form, R1 and R2 form, together with the nitrogen atom that bears them, a piperazinium group optionally substituted by one or more groups identical or different chosen from a hydroxy group or a $C_1$-$C_4$ (hydroxy)alkyl group.

According to a second preferred form of this variant, R1 and R2 form, together with the nitrogen atom that bears them, a pyrrolidine or piperidine group, substituted by a cationic —N⁺RaRbRc group, Ra, Rb, Rc identical or different, representing a $C_1$-$C_6$ alkyl group that can be substituted by a hydroxy and preferably chosen from trimethylammonium, triethylammonium, dimethyl-ethyl ammonium, diethylmethylammonium, diisopropylmethylammonium, diethyl-propyl ammonium, hydroxyethyl diethyl ammonium, di-beta-hydroxyethylmethylammonium, tri-beta-hydroxyethylammonium and in particular the pyrrolidine group or piperidine group, substituted by a tri($C_1$-$C_4$)alkyl ammonium group.

According to a particularly preferred form, R1 and R2 form, together with the nitrogen atom that bears them, a pyrrolidine or piperidine group, substituted by a group chosen from trimethylammonium, triethylammonium, dimethylethyl ammonium, diethylmethylammonium.

Preferably, the meta-phenylenediamines having general formula (I) according to the invention are chosen from the following compounds:

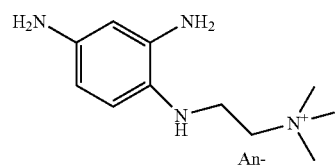

2-[(2,4-diaminophenyl)amino]-N,N,N-trimethylethanaminium, An⁻

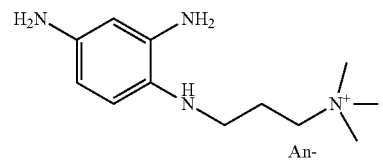

3-[(2,4-diaminophenyl)amino]-N,N,N-trimethylpropan-1-aminium, An⁻

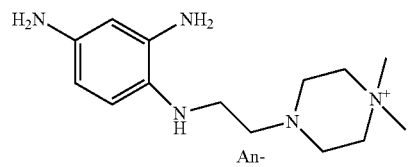

4-{2-[(2-amino-5-hydroxyphenyl)amino]ethyl}-1,1-dimethylpiperazin-1-ium, An⁻

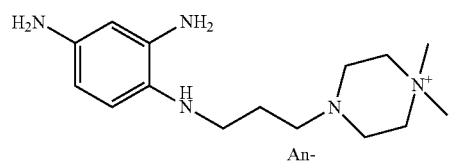

4-{3-[(2,4-diaminophenyl)amino]propyl}-1,1-dimethylpiperazin-1-ium, An⁻

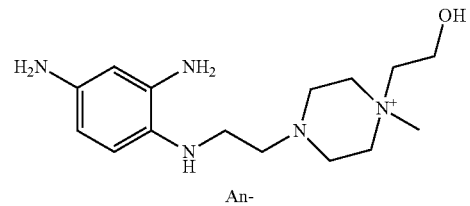

4-{2-[(2,4-diaminophenyl)amino]ethyl}-1-(2-hydroxyethyl)-1-methylpiperazin-1-ium, An⁻

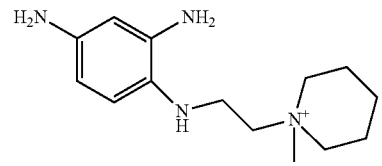

1-{2-[(2,4-diaminophenyl)amino]ethyl}-1-methylpiperidinium, An⁻

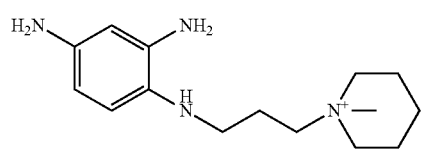

1-{3-[2,4-diaminophenyl)amino]propyl}-1-methylpiperidinium, An⁻

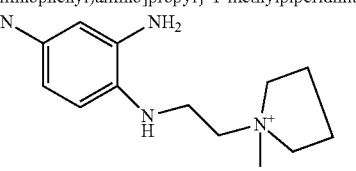

1-{2-[(2,4-diaminophenyl)amino]ethyl}-1-methylpyrrolidinium, An⁻

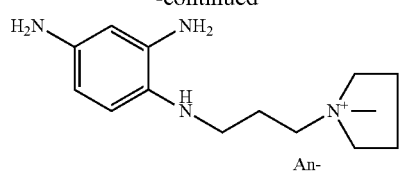

1-{3-[2,4-diaminophenyl)amino]propyl}-
1-methylpyrrolidinium, An-

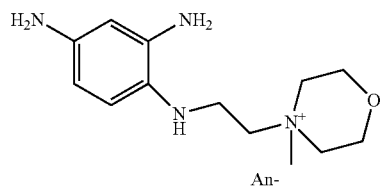

4-{2-[(2,4-diaminophenyl)amino]ethyl}-4-
methylmorpholin-4-ium, An-

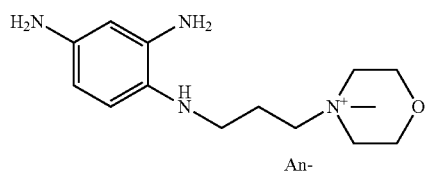

4-{3-[2,4-diaminophenyl)amino]propyl}-
4-methylmorpholin-4-ium, An-

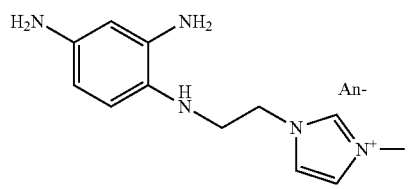

1-{2-[(2,4-diaminophenyl)amino]ethyl}-3-
methyl-1H-imidazol-3-ium, An-

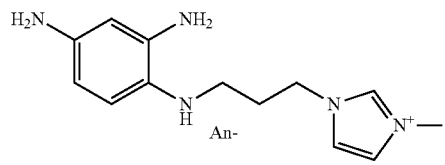

1-{3-[(2,4-diaminophenyl)amino]propyl}-
3-methyl-1H-imidazol-3-ium, An-

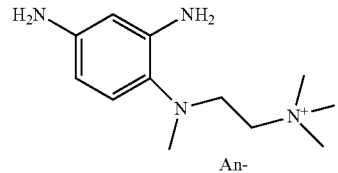

2-[(2,4-diaminophenyl)(methyl)amino]-
N,N,N-trimethylethanaminium, An-

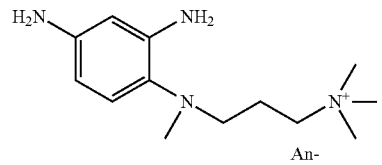

3-[(2,4-diaminophenyl)(methyl)amino]-
N,N,N-trimethylpropan-1-aminium, An-

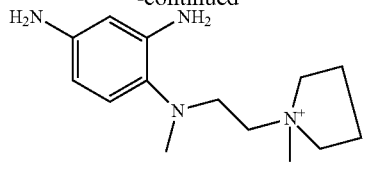

1-{2-[(2,4-
diaminophenyl)methyl)amino]ethyl}-1-
methylpyrrolidinium, An-

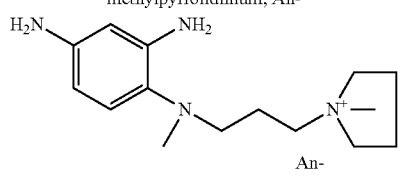

1-{3-[(2,4-
diaminophenyl)(methyl)amino]propyl}-1-
methylpyrrolidinium, An-

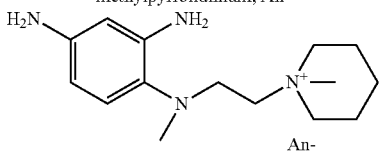

1-{2-[(2,4-
diaminophenyl)(methyl)amino]ethyl}-1-
methylpiperidinium, An-

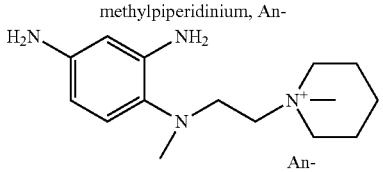

1-{3-[(2,4-
diaminophenyl)(methyl)amino]propyl}-1-
methylpiperidinium, An-

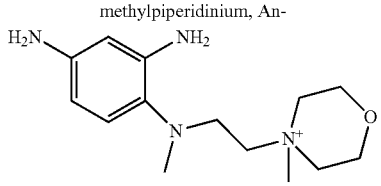

4-{2-[(2,4-
diaminophenyl)(methyl)amino]ethyl}-4-
methylmorpholin-4-ium, An-

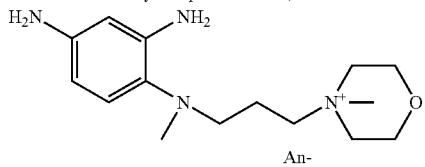

4-{3-[(2,4-
diaminophenyl)(methyl)amino]propyl}-4-
methylmorpholin-4-ium, An-

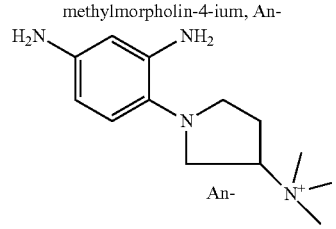

1-(2,4-diaminophenyl)-N,N,N-
trimethylpyrrolidin-3-aminium, An-

-continued

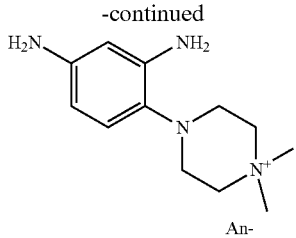

4-(2,4-diaminophenyl)-1,1-
dimethylpiperazin-1-ium, An-

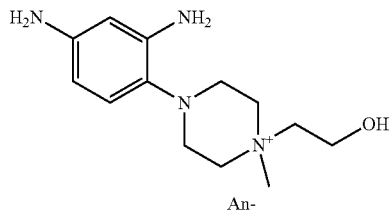

4-(2,4-diaminophenyl)-1-(2-hydroxyethyl)-
1-methylpiperazin-1-ium, An-

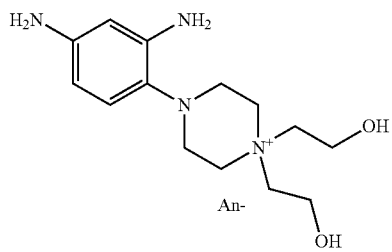

4-(2,4-diaminophenyl)-1,1-bis(2-
hydroxyethyl)piperazin-1-ium, An-

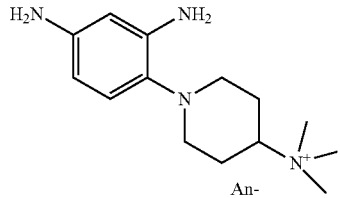

1-(2,4-diaminophenyl)-N,N,N-
trimethylpiperidin-4-aminium, An-

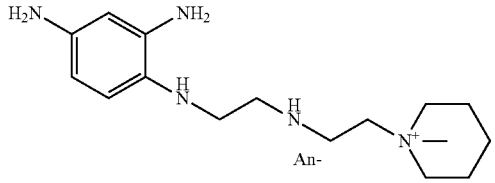

1-[2-({2-[(2,4-
diaminophenyl)amino]ethyl}amino)ethyl]-
1-methylpiperidinium, An-

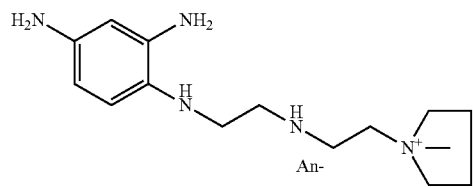

1-[2-({2-[(2,4-
diaminophenyl)amino]ethyl}amino)ethyl]-
1-methylpyrrolidinium,, An- -continued

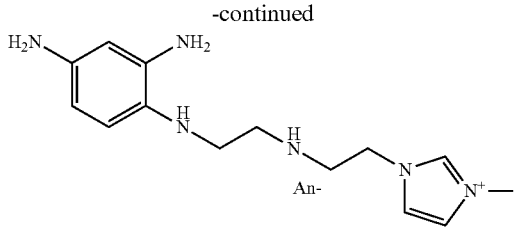

1-[2-({2-[(2,4-
diaminophenyl)amino]ethyl}amino)ethyl]-
3-methyl-1H-imidazol-3-ium, An-

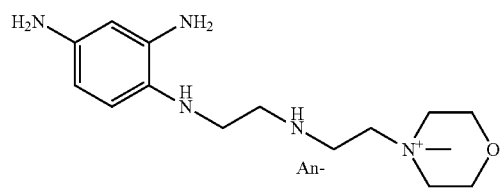

4-[2-({2-[(2-amino-5-4-[2-({2-[(2,4-
diaminophenyl)amino]ethyl}amino)ethyl]-
4-methylmorpholin-4-ium, An-

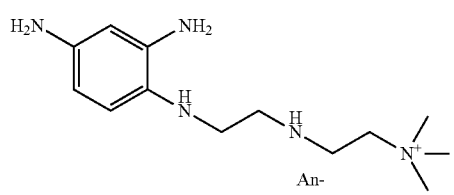

2-({2-[(2,4-
diaminophenyl)amino]ethyl}amino)-
N,N,N-trimethylethanaminium, An-

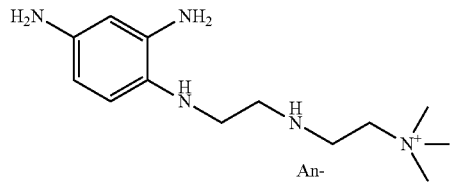

3-({2-[(2,4-
diaminophenyl)amino]ethyl}amino)-
N,N,N-trimethylpropan-1-aminium, An-

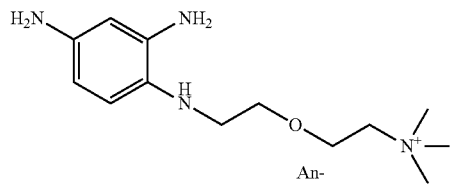

2-{2-[(2,4-diaminophenyl)amino]ethoxy}-
N,N,N-trimethylethanaminium, An-

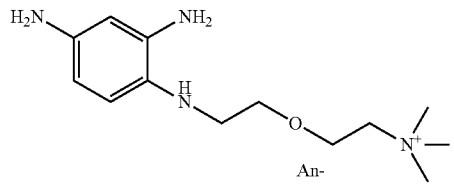

3-{2-[(2,4-diaminophenyl)amino]ethoxy}-
N,N,N-trimethypropan-1-aminium, An-

-continued

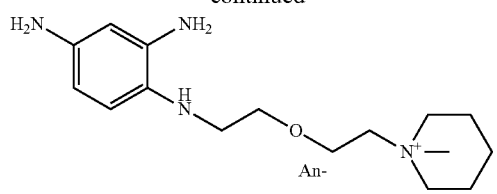

1-(2-{2-[(2,4-diaminophenyl)amino]ethoxy}ethyl)-1-methypiperidinium, An-

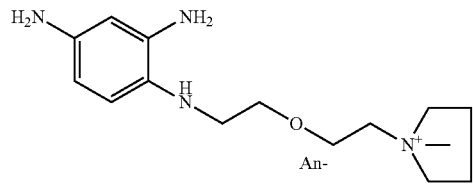

1-(2-{2-[(2,4-diaminophenyl)amino]ethoxy}ethyl)-1-methypyrrolidinium, An-

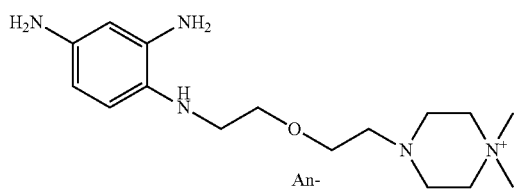

4-(2-{2-[(2,4-diaminophenyl)amino]ethoxy}ethyl)-1,1-dimethylpiperazin-1-ium, An-

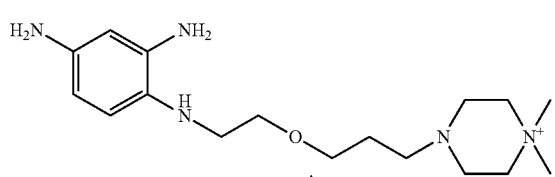

4-(3-{2-[(2,4-diaminophenyl)amino]ethoxy}propyl)-1,1-dimethylpiperazin-1-ium, An-

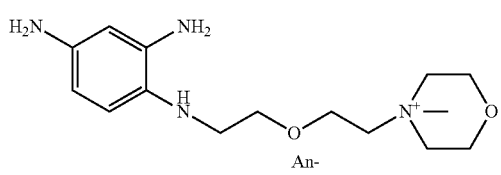

4-(2-{2-[(2,4-diaminophenyl)amino]ethoxy}ethyl)-4-methylmorpholin-4-ium, An-

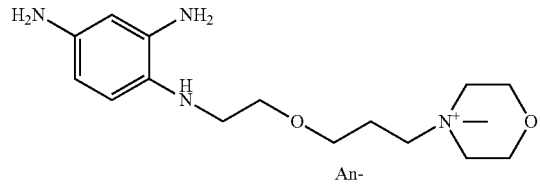

4-(3-{2-[(2,4-diaminophenyl)amino]ethoxy}propyl)-4-methylmorpholin-4-ium, An-

-continued

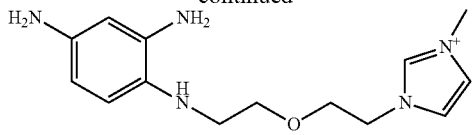

1-(2-{2-[(2,4-diaminophenyl)amino]ethoxy}ethyl)-3-methyl-1H-imidazol-3-ium, An-

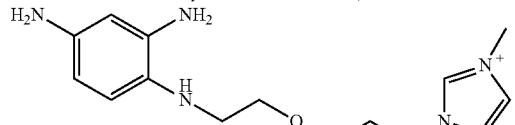

1-(3-{2-[(2,4-diaminophenyl)amino]ethoxy}propyl)-3-methyl-1H-imidazol-3-ium, Anand also the salts and/or solvates or isomers thereof, An⁻ having the same meaning as before.

According to one particularly preferred embodiment, the meta-phenylenediamine compound is chosen from compounds having the following formula (I), the addition salts thereof and the solvates thereof:

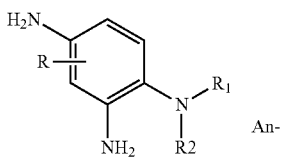

in which
R represents a hydrogen atom,
R1 and R2 form, together with the nitrogen atom that bears them, a 5- to 8-membered heterocyclic group of which one member is a quaternary ammonium, said heterocycle being optionally substituted by one or more groups, identical or different, chosen from a hydroxy group or a $C_1$-$C_4$ (hydroxy)alkyl group,
R' represents a hydrogen atom or a $C_1$-$C_4$ alkyl group, preferably a hydrogen atom,
An⁻ represents an anion or a mixture of anions which are organic or inorganic and cosmetically acceptable.

In particular, R1 and R2 form, together with the nitrogen atom that bears them, a pyrrolidine or piperidine group, substituted by a cationic —N⁺ RaRbRc group, Ra, Rb, Rc identical or different, representing a $C_1$-$C_6$ alkyl group that can be substituted by a hydroxy and preferably chosen from trimethylammonium, triethylammonium, dimethyl-ethyl ammonium, diethylmethylammonium, diisopropylmethylammonium, diethyl-propyl ammonium, hydroxyethyl diethyl ammonium, di-beta-hydroxyethylmethylammonium, tri-beta-hydroxyethylammonium and in particular the pyrrolidine group or piperidine group, substituted by a tri($C_1$-$C_4$) alkyl ammonium group.

More preferably, R1 and R2 form, together with the nitrogen atom that bears them, a pyrrolidine or piperidine group, substituted by a group chosen from trimethylammonium, triethylammonium, dimethyl-ethyl ammonium, diethylmethylammonium.

More preferably, the meta-phenylenediamine compound having formula (I) is chosen from 4-(2,4-diaminophenyl)-1,1-dimethylpiperazin-1-ium, An⁻, salts thereof and solvates thereof.

Dyeing Composition

Another subject of the invention is a composition for dyeing keratin fibres comprising, in a suitable medium, at least one compound having formula (I) as defined above.

The compound having formula (I) may be present in the composition in an amount of between 0.001% and 10%, preferably between 0.005% and 6%, by weight approximately of the total weight of the dye composition.

The composition may also comprise at least one oxidation base. These bases may especially be chosen from para-phenylenediamines, bis(phenyl)alkylenediamines, para-aminophenols, ortho-aminophenols and heterocyclic bases, and the addition salts thereof.

Among para-phenylenediamines, as examples mention may be more particularly made of para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl 3-methyl aniline, N,N-bis-(β-hydroxyethyl)-para-phenylenediamine, 4-N,N-bis-(β-hydroxyethyl)amino-2-methyl-aniline, 4-N, N-bis-(β-hydroxyethyl)amino-2-chloro-aniline, 2-β-hydroxyethyl-para-phenylenediamine, 2-fluoro-para-phenylenediamine, 2-isopropyl para-phenylenediamine, N-(β-hydroxypropyl)-para-phenylenediamine, 2-hydroxymethyl-para-phenylenediamine, la N,N-dimethyl-3-methyl-para-phenylenediamine, N,N-(ethyl,-β-hydroxyethyl)-para-phenylenediamine, N-(β,γ-dihydroxypropyl) para-phenylenediamine, N-(4'-aminophenyl)-para-phenylenediamine, la N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenyl-pyrrolidine, 2-thienyl-para-phenylene diamine, 2-β hydroxyethylamino-5-amino-toluene, 3-hydroxy 1-(4' aminophenyl)pyrrolidine, 6-(4-amino-phenylamino)-hexan-1-ol, N-(4-amino-3-methylphenyl)-N-[3-(1H-imidazol-1-yl)-propyl]-amine, N-(4-amino-phenyl)-N-[3-(1H-imidazol-1-yl)-propyl]-amine and the addition salts thereof with an acid.

Among the para-phenylenediamines mentioned above, para-phenylenediamine, la para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis-(β-hydroxyethyl)-para-phenylenediamine, 2-chloro-para-phenylenediamine, 2-β-acetylaminoethyloxy-para-phenylenediamine, 2-[{2-[(4-aminophenyl)amino]ethyl}(2-hydroxyethyl)amino]ethanol and the addition salts thereof with an acid are particularly preferred.

Among the bisphenylalkylenediamines, mention may be made, by way of example, of N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl) ethylenediamine and 1,8-bis(2,5-diaminophenoxy)-3,6-dioxaoctane, and the addition salts thereof with an acid.

Among the para-aminophenols, mention may be made, by way of example, of para-aminophenol, 4-amino-3-methylphenol, 4-amino-3-fluorophenol, 4-amino-2-chlorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 4-amino-2,6-dichlorophenol, 4-amino-6-[((5'-amino-2'-hydroxy-3'-methyl)phenyl)methyl]-2-methylphenol, bis[(5'-amino-2'-hydroxy)phenyl]methane and the addition salts thereof with an acid.

Among the ortho-aminophenols, mention may be made, by way of example, of 2-aminophenol, 2-amino-5-methylphenol, 2-amino-6-methylphenol and 5-acetamido-2-aminophenol, and the addition salts thereof with an acid.

Among the heterocyclic bases, mention may be made, by way of example, of pyridine derivatives, pyrimidine derivatives and pyrazole derivatives.

The pyridine derivatives include the compounds described, for instance, in patents GB 1 026 978 and GB 1 153 196, such as 2,5-diaminopyridine, 2-(4-methoxyphenyl)amino-3-aminopyridine, 3,4-diaminopyridine, and the addition salts thereof with an acid.

Other pyridine oxidation bases of use in the present invention are the 3-aminopyrazolo[1,5-a]pyridine oxidation bases or addition salts thereof described, for instance, in patent application FR 2 801 308. Mention may be made, by way of example, of pyrazolo[1,5-a]pyrid-3-ylamine, 2-(acetylamino)pyrazolo[1,5-a]pyrid-3-ylamine, 2-(morpholin-4-yl) pyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-(morpholin-4-yl)pyrazolo[1,5-a]pyrid-3-ylamine, pyrazolo[1,5-a]pyridine-3,5-diamine, 5-(morpholin-4-yl)pyrazolo[1,5-a]pyrid-3-ylamine, 2-[(3-aminopyrazolo[1,5-a]pyrid-5-yl)(2-hydroxyethyl)amino] ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol, 3-aminopyrazolo[1,5-a]pyridin-7-ol and the addition salts thereof with an acid.

Among the pyridine bases that are of use in the present invention, mention may also be made of the compounds described in patent applications EP 1792903 and EP 1792606 and the addition salts thereof.

Mention may be made, among pyrimidine derivatives, of the compounds described, for instance, in patents DE 2359399, JP 88-169571, JP 05-63124 and EP 0 770 375 or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine and the addition salts thereof and the tautomeric forms thereof, when a tautomeric equilibrium exists.

Among the pyrazolopyrimidine derivatives, mention may be made of the compounds described, for instance, in patent applications EP 0847271, EP 0926149 and EP 1147109 and the addition salts thereof.

Among the pyrazole derivatives that may be mentioned are the compounds described in patents DE 3843892, DE 4133957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triamino-pyrazole, 1-methyl-3,4,5-triaminopyrazole, 3,5-diamino-1-methyl-4-methylaminopyrazole, 3,5-diamino-4-(β-hydroxyethyl)amino-1-methylpyrazole, and the addition salts thereof.

By way of oxidation bases, mention may also be made of the diamino-N,N-dihydropyrazolone derivatives having formula (III) or one of the addition salts or solvates thereof:

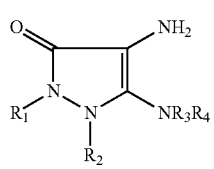

(III)

wherein:

$R_1$, $R_2$, $R_3$ and $R_4$, which may be identical or different, represent:
 a straight or branched $C_1$-$C_6$ alkyl group which is optionally substituted by one or more groups chosen from the group consisting of an $OR_5$ group, a $NR_6R_7$ group, a carboxyl group, a sulfonyl group, a carboxamide $CONR_6R_7$ group, a sulfonamide $SO_2NR_6R_7$ group, a heteroaryl, an aryl optionally substituted by a ($C_1$-$C_4$)alkyl group, a hydroxyl, a $C_1$-$C_2$ alkoxy, an amino, a di($C_1$-$C_2$)alkylamino;
 an aryl group optionally substituted by one or more ($C_1$-$C_4$)alkyl, hydroxyl, $C_1$-$C_2$ alkoxy, amino or di($C_1$-$C_2$)alkylamino;
 a 5- or 6-membered heteroaryl group, optionally substituted by one or more groups chosen from ($C_1$-$C_4$) alkyl and ($C_1$-$C_2$)alkoxy;
$R_3$ and $R_4$ may also represent a hydrogen atom;
$R_5$, $R_6$ and $R_7$ are identical or different and represent a hydrogen atom; a straight or branched $C_1$-$C_4$ alkyl group which is optionally substituted by one or more groups chosen from the group consisting of a hydroxyl, a $C_1$-$C_2$ alkoxy, a carboxamide $CONR_8R_9$, a sulfonyl $SO_2R_8$, an aryl optionally substituted by a ($C_1$-$C_4$)alkyl, a hydroxyl, a $C_1$-$C_2$ alkoxy, an amino, a di($C_1$-$C_2$)alkylamino; an aryl optionally substituted by a ($C_1$-$C_4$)alkyl, a hydroxyl, a $C_1$-$C_2$ alkoxy, an amino, a di($C_1$-$C_2$)alkylamino;
$R_6$ and $R_7$ are identical or different and may also represent a $CONR_8R_9$ carboxamide group or a sulfonyl $SO_2R_8$;
$R_8$ and $R_9$ are identical or different and represent a hydrogen atom or a straight or branched $C_1$-$C_4$ alkyl group which is optionally substituted by one or more of hydroxyl, $C_1$-$C_2$ alkoxy;

$R_1$ and $R_2$, on the one hand, and $R_3$ and $R_4$, on the other hand, may form, with the nitrogen atoms to which they are attached, a saturated or unsaturated heterocycle containing 5 to 7 members which is optionally substituted by one or more groups chosen from the group consisting of halogen atoms, amino, di($C_1$-$C_4$)alkylamino, hydroxyl, carboxyl, carboxamide and ($C_1$-$C_2$)alkoxy groups, $C_1$-$C_4$ alkyl groups optionally substituted by one or more hydroxyl, amino, (di)alkylamino, alkoxy, carboxyl or sulfonyl groups;

$R_3$ and $R_4$ may also form, together with the nitrogen atom to which they are attached, a 5- or 7-membered heterocycle in which the carbon atoms may be replaced by an optionally substituted nitrogen or oxygen atom.

These diamino-N,N-dihydropyrazolone derivatives are described more particularly in application FR 2866338, and one particularly preferred derivative is 2,3-diamino-6,7-dihydro-1H,5H-pyrazolo[1,2-a]pyrazol-1-one dimethanesulfonate.

Oxidation bases further include diamino-N,N-dihydropyrazolone derivatives having formula (IV) or one of the addition salts or solvates thereof:

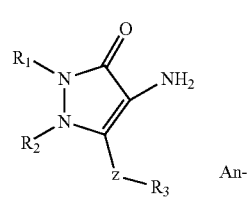

(IV)

in which:
 z represents independently:
  a covalent single bond,
  a divalent group chosen from
  an oxygen atom,
  a group —$NR_6$—, where $R_6$ represents a hydrogen atom or a $C_1$-$C_6$ alkyl group, or $R_6$ with $R_3$, together with the nitrogen atom to which they are attached, form a 5- to 8-membered heterocycle which is unsubstituted or substituted, saturated or unsaturated, aromatic or non-aromatic, and optionally contains one or more other heteroatoms or substituents chosen from N, O, S, $SO_2$, —CO—, it being possible for the heterocycle to be cationic and/or to be substituted by a cationic group,
  a —$N^+R_7R_8$— group where $R_7$ and $R_8$ independently represent an alkyl group; the alkyl group may be substituted by an OH or an —Oalkyl,
 $R_3$ represents:
  a hydrogen
  a $C_1$-$C_{10}$ alkyl group which is optionally substituted, it being possible for the alkyl group to be interrupted with a heteroatom or a substituent chosen from O, N, Si, S, SO and $SO_2$,
  a $C_1$-$C_{10}$ alkyl group which is substituted and/or interrupted with a cationic group,
  a halogen,
  an $SO_3H$ group,
  a 5- to 8-membered ring which is substituted or unsubstituted, saturated or unsaturated or aromatic and optionally contains one or more heteroatoms or substituents chosen from N, O, S, $SO_2$, —CO, it being possible for the ring to be cationic and/or to be substituted by a cationic group, $R_1$ and $R_2$, which may be identical or different, represent:
- a straight or branched $C_1$-$C_6$ alkyl group which is optionally substituted by one or more groups chosen from a group $OR_5$, a group $NR_9R_{10}$, a carboxyl group, a sulfonyl group, a carboxamide group $CONR_9R_{10}$; a sulfonamide group $SO_2NR_9R_{10}$, a heteroaryl, an aryl which is optionally substituted by a ($C_1$-$C_4$)alkyl, hydroxyl, $C_1$-$C_2$ alkoxy, amino or di($C_1$-$C_2$)alkylamino group;
- an aryl group optionally substituted by one or more ($C_1$-$C_4$)alkyl, hydroxyl, $C_1$-$C_2$ alkoxy, amino or di($C_1$-$C_2$)alkylamino;
- a 5- or 6-membered heteroaryl group which is optionally substituted by one or more groups chosen from ($C_1$-$C_4$)alkyl which is monosubstituted or polysubstituted by an OH or an —Oalkyl, ($C_1$-$C_2$)alkoxy;

$R_1$ and $R_2$ may form, with the nitrogen atoms to which they are attached, a saturated or unsaturated heterocycle containing 5 to 7 members which is optionally substituted by one or more groups chosen from the group consisting of halogen atoms, amino, di($C_1$-$C_4$)alkylamino, hydroxyl, carboxyl, carboxamide and ($C_1$-$C_2$)alkoxy groups, and $C_1$-$C_4$ alkyl groups which are optionally substituted by one or more hydroxyl, amino, (di)alkylamino, alkoxy, carboxyl or sulfonyl groups, An⁻ represents an anion or a group of anions making it possible to ensure the electroneutrality of the compounds having formula (IV), on the condition that at least one of the groups Z and $R_3$ represents a cationic group.

These derivatives of diamino-N,N-dihydropyrazolone are described in patent application FR 2 927 078.

In general, the concentration of the oxidation base(s) ranges from 0.0001% to 20% and preferably from 0.005% to 6% by weight, relative to the total weight of the composition.

Couplers

The dye composition according to the invention may contain and preferably contains one or more additional oxidation couplers, different than the compounds having general formula (I), that are conventionally used for dyeing keratin fibres. Among these couplers, mention may be made especially of meta-phenylenediamines, meta-aminophenols, meta-diphenols, naphthalene couplers and heterocyclic couplers, and the addition salts thereof.

Examples of a coupler that may be mentioned include 2-methyl-5-aminophenol, 5-N-(β-hydroxyethyl)amino-2-methylphenol, 6-chloro-2-methyl-5-aminophenol, 3-aminophenol, 2,4-dichloro-3-aminophenol, 5-amino-4-chloro-o-cresol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 1,5-dihydroxynaphthalene, 2,7-naphthalenediol, 1-acetoxy-2-methylnaphthalene, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 2,6-dihydroxy-3-4-dimethylpyridine, 3-amino-2-methylamino-6-methoxypyridine, 1-N-(β-hydroxyethyl)amino-3,4-methylenedioxybenzene, 2,6-bis(β-hydroxyethylamino)toluene and 3-methyl-1-phenyl-5-pyrazolone and the addition salts thereof with an acid.

In the dye composition of the present invention, the coupler(s), if it (they) is (are) present, generally represent(s) an amount of between 0.001% and 10% by weight, preferably between 0.005% and 6% by weight approximately of the total weight of the composition.

The dye composition in accordance with the invention may also contain one or more direct dyes that may in particular be chosen from nitrobenzene dyes, azo direct dyes and methine direct dyes. These direct dyes may be of nonionic, anionic or cationic nature.

The medium that is suitable for dyeing, also known as the dye support, generally comprises water or a mixture of water and one or more solvents, for instance $C_1$-$C_4$ lower alcohols such as ethanol and isopropanol, polyols such as propyleneglycol, dipropyleneglycol or glycerol, and polyol ethers such as dipropyleneglycol monomethylether.

The solvent(s) is (are) generally present in proportions that may be between 1% and 40% by weight approximately and more preferably between 3% and 30% by weight approximately relative to the total weight of the dye composition.

The dye composition in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, and in particular anionic, cationic, nonionic and amphoteric polymeric associative thickeners, antioxidants, penetrants, sequestrants, fragrances, buffers, dispersants, conditioning agents, for instance volatile or non-volatile, modified or unmodified silicones, film-forming agents, ceramides, preserving agents and opacifiers.

The above adjuvants are generally present in an amount, for each of them, of between 0.01% and 20% by weight relative to the weight of the composition.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The pH of the dye composition in accordance with the invention is generally between 3 and 12 approximately and preferably between 5 and 11 approximately. It may be adjusted to the desired value by means of acidifying or basifying agents customarily used in the dyeing of keratin fibres, or alternatively using standard buffer systems.

Among the acidifying agents, mention made be made, by way of example, of inorganic or organic acids, for instance hydrochloric acid, orthophosphoric acid, sulfuric acid, carboxylic acids, for instance acetic acid, tartaric acid, citric acid and lactic acid, and sulfonic acids.

Among the basifying agents, mention made be made, by way of example, of aqueous ammonia, alkali metal carbonates, alkanolamines, such as mono-, di- and triethanolamines and derivatives thereof, sodium hydroxide, potassium hydroxide and the compounds having formula (III) below:

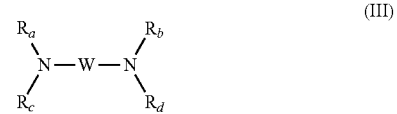

(III)

in which W is a propylene residue optionally substituted by a hydroxyl substituent or a $C_1$-$C_4$ alkyl group; $R_a$, $R_b$, $R_c$ and $R_d$, which may be identical or different, represent a hydrogen atom or a $C_1$-$C_4$ alkyl or $C_1$-$C_4$ hydroxyalkyl group.

The composition according to the invention may comprise one or more oxidizing agents.

The oxidizing agents are those conventionally used for the oxidation dyeing of keratin fibres, for instance hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. Hydrogen peroxide is particularly preferred.

The dye composition with or without oxidizing agent according to the invention may be in various forms, such as in the form of liquids, creams or gels, or in any other form that is suitable for dyeing keratin fibres, and especially human hair.

It may result from the mixing, at the time of use, of several compositions.

In particular, it results from the mixing of at least two compositions, one comprising at least one compound having formula (I), optionally one or more oxidation bases, optionally one or more additional couplers other than the compounds having formula (I) or salts thereof, and a second composition comprising one or more oxidizing agents as described above.

The composition of the invention is thus applied to the hair for the dyeing of keratin fibres, either as is or in the presence of one or more oxidizing agents for the dyeing of keratin fibres.

The process of the present invention is a process in which the composition according to the present invention as defined previously is applied to the fibres, either alone or in the presence of an oxidizing agent, for a time that is sufficient to develop the desired colour. The colour may be developed at acidic, neutral or alkaline pH, and the oxidizing agent may be added to the composition of the invention just at the time of use, or it may be used starting from an oxidizing composition which comprises it and which is applied simultaneously with or sequentially to the composition of the invention.

In one particular embodiment, the composition is devoid of oxidizing agent and is mixed, preferably at the time of use, with a composition containing, in a medium appropriate for dyeing, one or more oxidizing agents, these oxidizing agents being present in an amount sufficient to develop a colour. The mixture obtained is then applied to the keratin fibres. After a leave-in time of approximately 3 to 50 minutes, preferably approximately 5 to 30 minutes, the keratin fibres are rinsed, washed with shampoo, rinsed again and then dried.

The oxidizing agents are those indicated above.

The oxidizing composition may also contain various adjuvants conventionally used in compositions for dyeing the hair and as defined above.

The pH of the oxidizing composition containing the oxidizing agent is such that, after mixing with the dye composition, the pH of the resulting composition applied to the keratin fibres preferably varies between 3 and 12 approximately and more preferably still between 5 and 11. It may be adjusted to the desired value by means of acidifying or basifying agents customarily used in the dyeing of keratin fibres and as defined above.

The ready-to-use composition which is ultimately applied to the keratin fibres may be in a variety of forms, such as in the form of liquids, creams or gels or any other form appropriate for carrying out dyeing of keratin fibres, and in particular of human hair.

Another subject of the invention is a dyeing "kit" or multi-compartment device in which a first compartment contains the dye composition devoid of oxidizing agent of the present invention defined above, comprising one or more oxidation bases chosen from the compound having formula (I) or the addition salts thereof with an acid, and a second compartment contains one or more oxidizing agents.

These devices may be equipped with a means for dispensing the desired mixture on the hair, such as the devices described in patent FR-2 586 913 in the name of the Applicant.

Preparation of the Compound Having Formula (I)

Compounds having formula (I) may be for instance synthesized according to the following procedures:

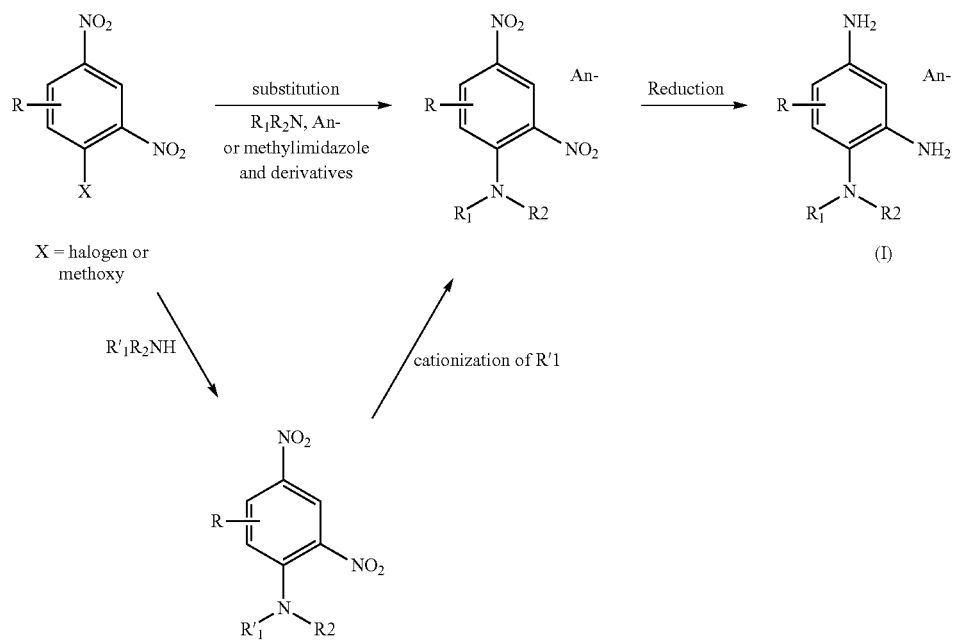

General procedure 2
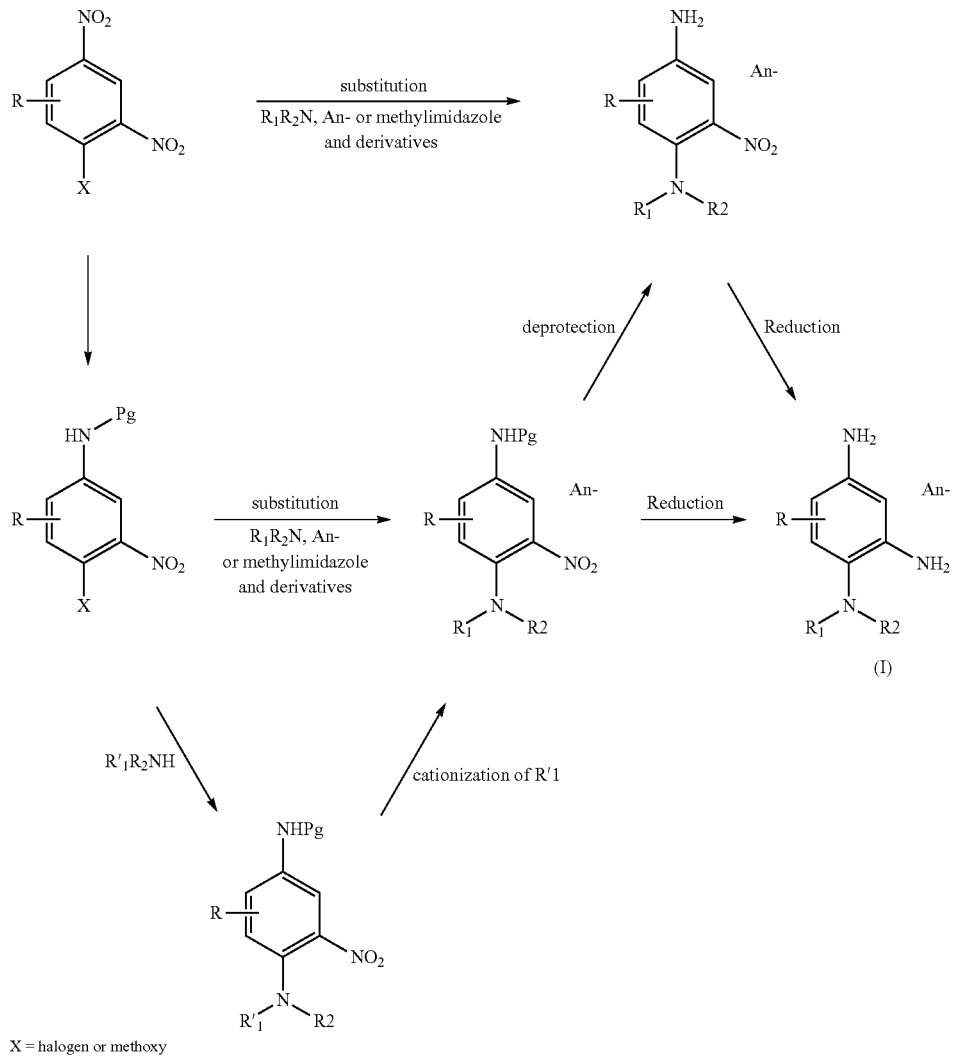
X = halogen or methoxy
Pg = amine-function protecting group
As an example, when $R_1$ represents a $C_1$-$C_{10}$ alkyl group substituted by a cationic group, said alkyl group being interrupted with one or more heteroatoms chosen from NR2 or O, then the method of synthesis used may be one of the three following:
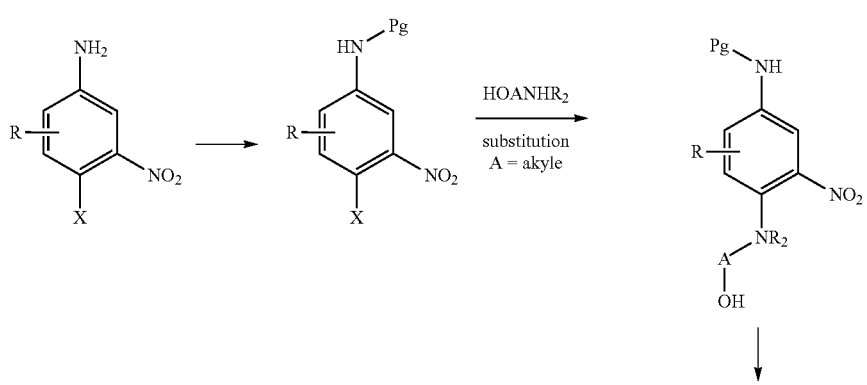

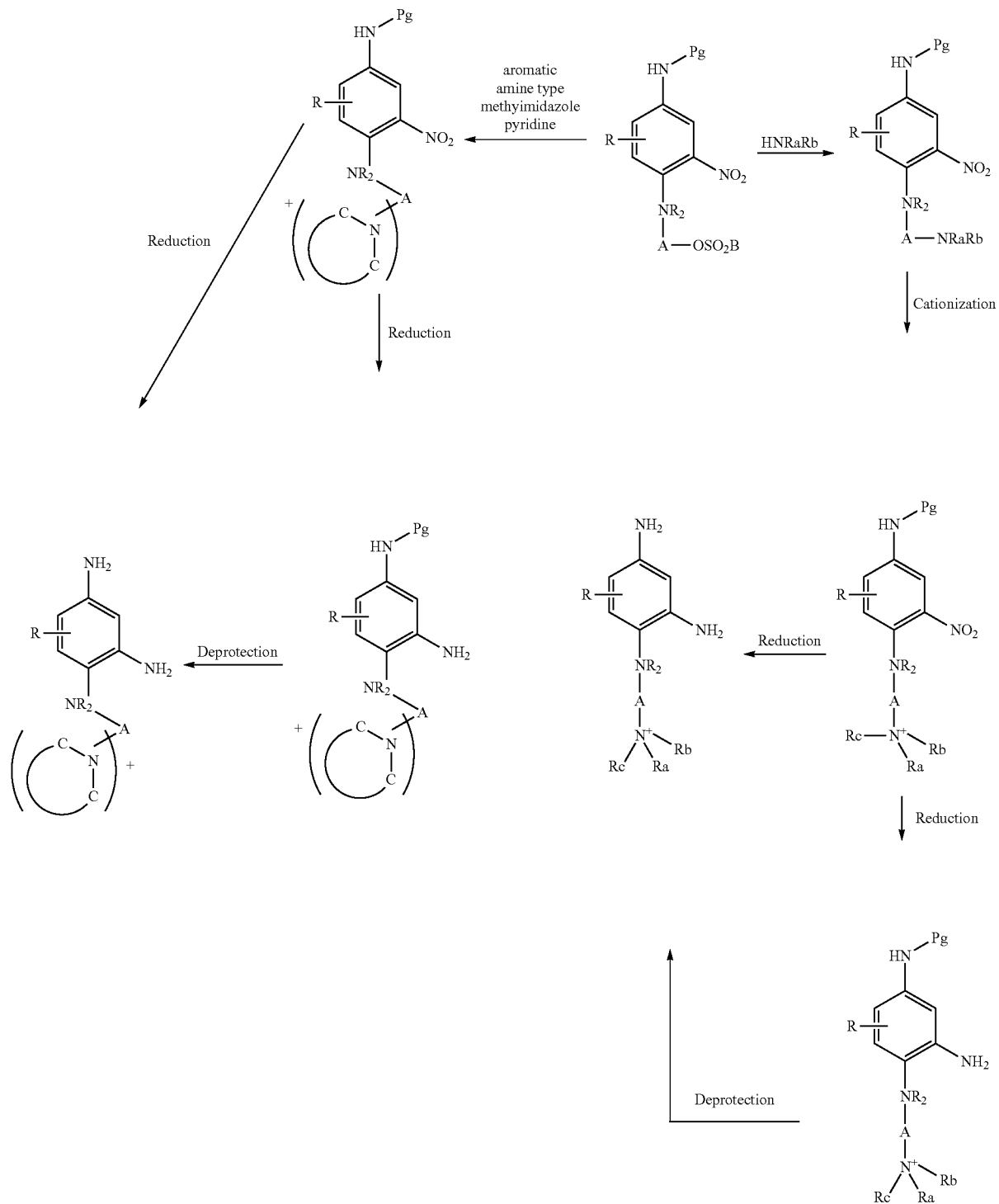
X = halogen or methoxy
A = alkyle
Pg : amine protection group
B = alkyle, hydroxyalkyle, phenyl, optionnally substituted

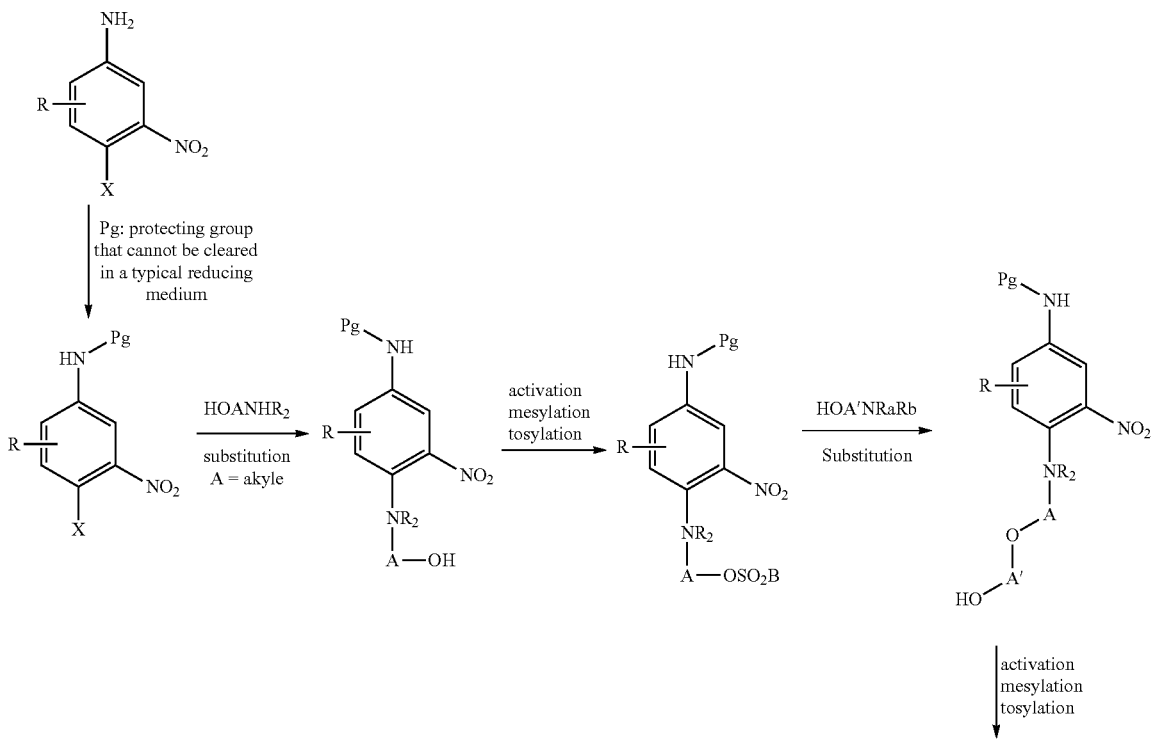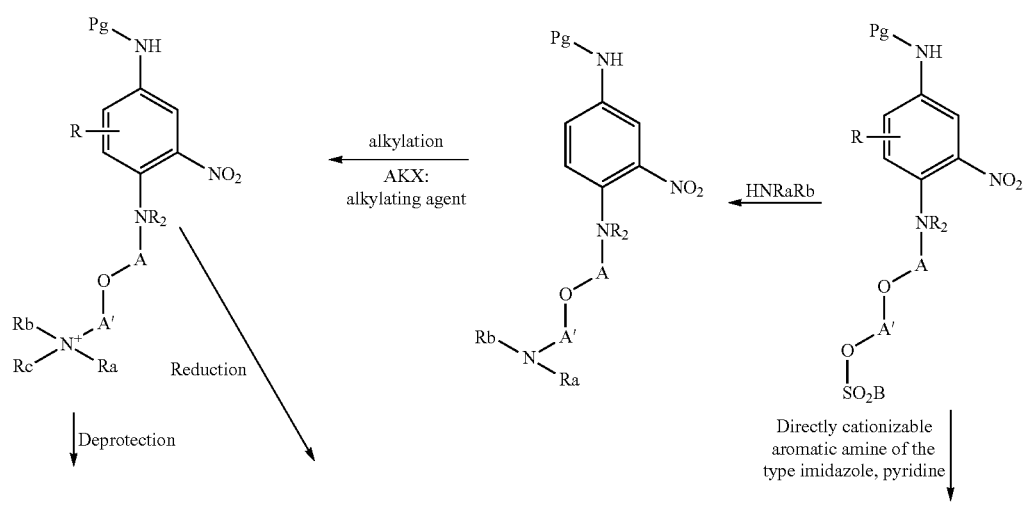

-continued
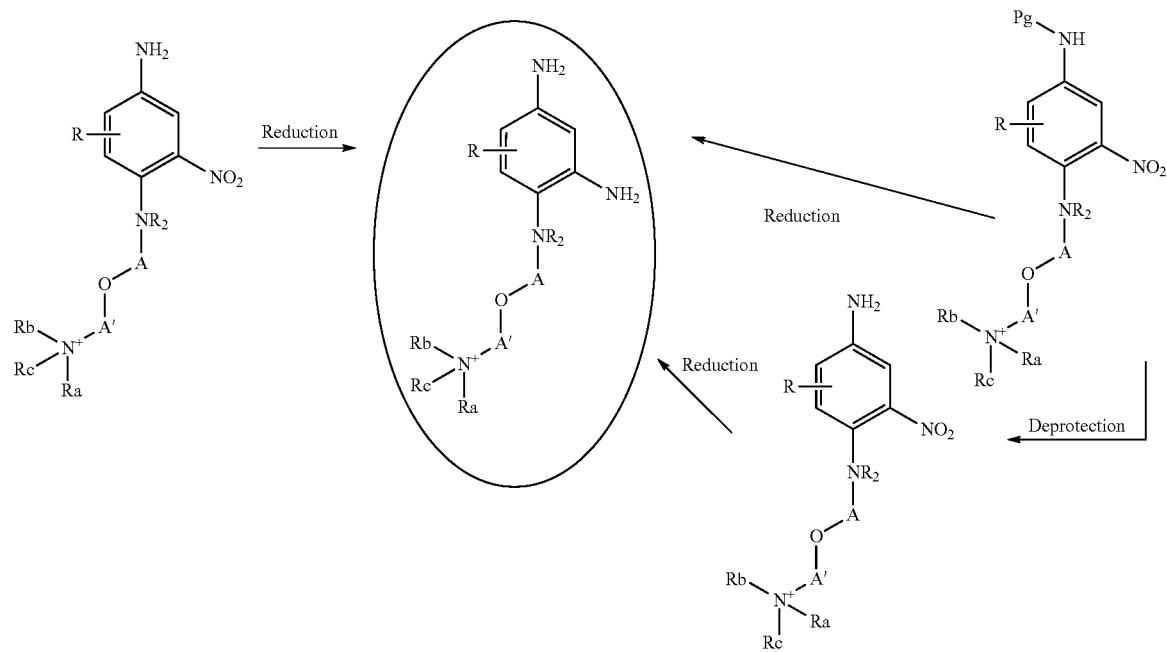
X = halogen or methoxy
B = alkyl, hydroxyalkyl, phenyl, optionally subsituted
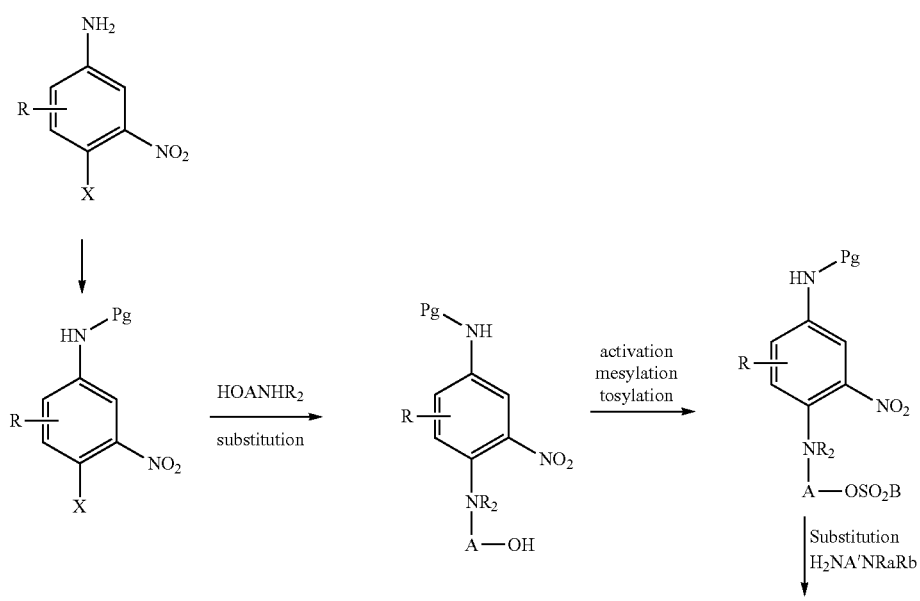

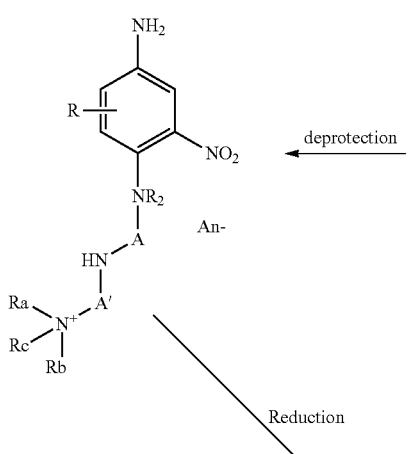
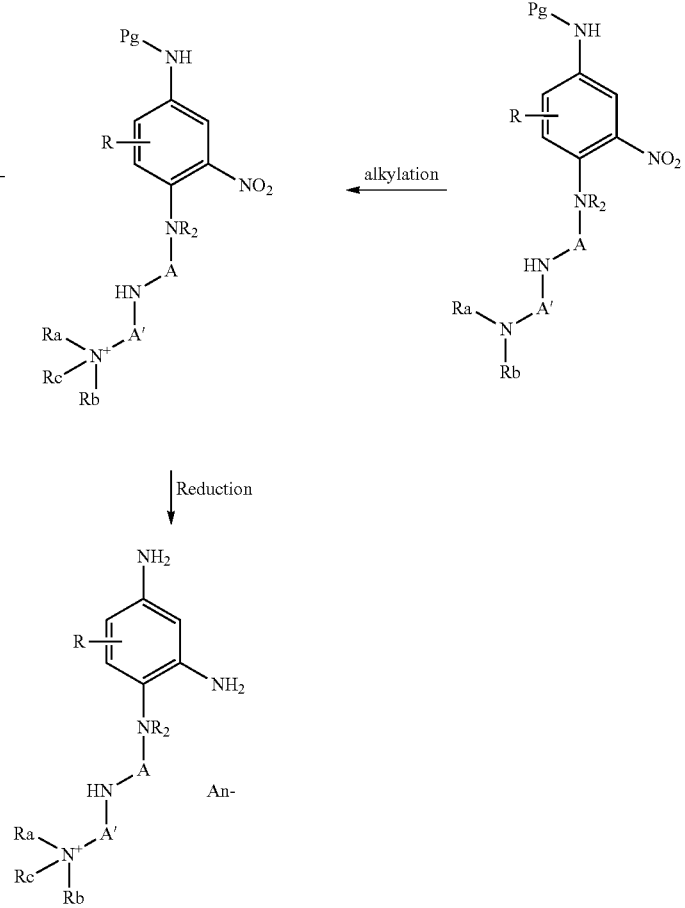

X = halogen or methoxy
B = alkyl, hydroxyalkyl, phenyl, optionally substitued
A and A' which are identical or differentrepresent a hydrocarbon-based chain The substitution reaction is performed in a dipolar solvent such as acetonitrile, THF or in DMF or NMP, or in an alcohol such as ethanol for instance, in the presence of a base such as triethylamine, ethyldiisopropylamine, sodium hydroxide or potassium hydroxide, for instance, and one or more HOAZ1H equivalents for 1 to 24 hours at a temperature from 20° C. to the reflux temperature of the solvent.

The hydroxyl function thus introduced is then substituted by a halide (for instance mesyl or tosyl halide) in a solvent such as acetonitrile, THF or in an alcohol such as ethanol, for instance, in the presence of a base such as triethylamine, ethyldiisopropylamine, sodium hydroxide or potassium hydroxide, for instance, for 1 to 24 hours at a temperature from 20° C. to the reflux temperature of the solvent.

The substitution of the leaving group introduced in the preceding step is performed either by reaction with an aromatic tertiary amine such as methylimidazole to lead directly to the cationic compounds, or by reaction with a particular primary or secondary amine, for instance N,N-dimethylethylenediamine or 2-piperidin-1-ylethanamine to lead to the compounds that are alkylated with at least one equivalent of alkyl halide or methyl sulfate in a solvent such as THF or acetonitrile or dioxane or ethyl acetate for 15 minutes to 24 hours at a temperature ranging from 15° C. to the reflux temperature of the solvent, to give the cationic nitro compounds.

The nitro substituent of these compounds is reduced under standard conditions, for instance by performing a hydrogenation reaction under heterogeneous catalysis in the presence of Pd/C, Pd(II)/C, Ni/Ra, etc., or alternatively by performing a reduction reaction with a metal, for instance with zinc, iron, tin, etc. (see *Advanced Organic Chemistry,* 3rd Edition, J. March, 1985, Wiley Interscience and *Reduction in Organic Chemistry*, M. Hudlicky, 1983, Ellis Horwood Series Chemical Science).

The examples which follow serve to illustrate the invention without, however, exhibiting a limiting nature.

EXAMPLES

Example of Synthesis

Synthesis of 4-(2,4-diaminophenyl)-1,1-dimethylpiperazin-1-ium chloride dihydrochloride

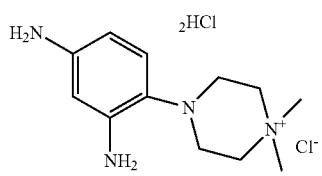

Synthesis of 1-(2,4-dinitrophenyl)-4-methylpiperazine

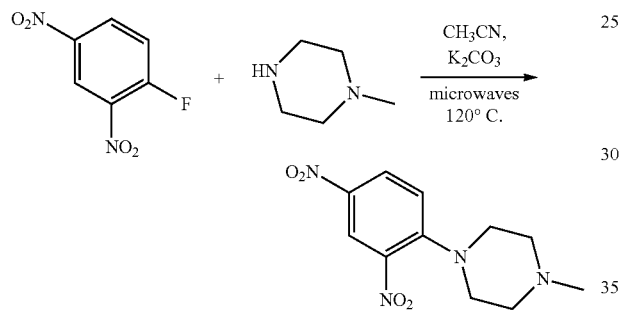

A 35-ml microwave reactor is successively charged with 10 ml of acetonitrile, 1 g (5.37 mmol) of 1-fluoro-2,4-dinitrobenzene, 0.89 g (6.44 mmol) of potassium carbonate and 0.65 ml (5.9 mmol) of 1-methylpiperazine. This medium is irradiated at 120° C. for 30 minutes. After cooling the medium is filtered through a sintered funnel and the solvent is evaporated until a yellow-brown residue is obtained.

This residue is purified by chromatography on a silica column (eluent=EtOAc/MeOH 95/5).

After evaporating the solvents, the expected compound is recovered in the form of an orange powder (6.76 g; yield 89.5%).

Analysis by mass spectrometry confirms the structure of the expected compound, $C_{11}H_{14}N_4O4$ is mainly detected.

The quasi-molecular ions $[M+H]^+$, $[M+Na]^+$, $[M-H]^-$ of the expected molecule are mainly detected.

Synthesis of 4-(2,4-dinitrophenyl)-1,1-dimethylpiperazin-1-ium methyl sulfate

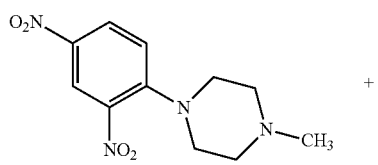

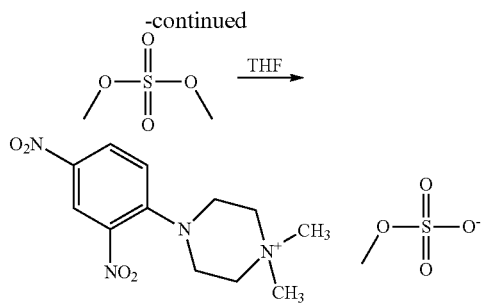

10 ml of THF and 1.35 g (5 mmol) of 1-(2,4-dinitrophenyl)-4-methylpiperazine are successively placed in a 25-ml three-necked flask equipped with a thermometer, a condenser, a bubbler and a dropping funnel, with magnetic stirring.

Next, added dropwise are 0.5 ml (5.25 mmol) of dimethyl sulfate and the whole assembly is held at room temperature with stirring for 3 hours.

The yellow solid formed is filtered off on a sintered glass funnel, drained by suction, washed with THF and then dried under vacuum at 50° C. in the presence of a desiccant, to constant weight. 2 g (quantitative yield) of the expected compound is thus isolated in the form of a yellow solid.

Analysis by mass spectrometry confirms the structure of the expected compound. The expected cation $C_{12}H_{17}N_4O_4$ and the counterion $(CH_3OSO^{3-})$ are mainly detected.

Synthesis of 4-(2-amino-5-hydroxyphenyl)-1,1-dimethylpiperazin-1-ium

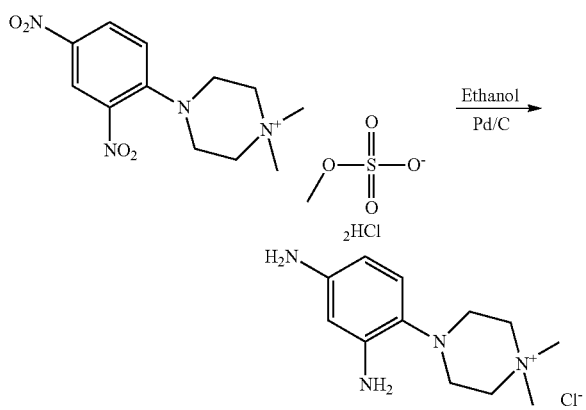

This reduction is carried out using a hydrogenation reactor of H-Cube type containing a 90×4 mm cartridge of 10% Pd/C.

A solution of 2 g (5 mmol) of 4-(2,4-dinitrophenyl)-1,1-dimethylpiperazin-1-ium methyl sulfate in 20 ml methanol is introduced under a flow rate of 4 ml per minute through a palladium on charcoal catalyst cartridge within the H-Cube system.

On leaving the device, the expected compound is isolated by precipitation in 2 ml of 6 N hydrochloric acid in isopropanol.

The solution obtained is evaporated to dryness until a yellow-beige powder is obtained.

After drying under vacuum at 30° C. in the presence of a desiccant, 2 g of beige solid is obtained (yield 97.1%) corresponding to the expected compound.

Analysis by mass spectrometry confirms the structure of the expected compound. The expected cation $C_{12}H_{21}N_4$ is mainly detected.

The NMR analysis complies.

Examples of Dyes

The following dye compositions are prepared:

| | | | |
|---|---|---|---|
| 4-(2,4-diaminophenyl)-1,1-dimethylpiperazin-1-ium chloride dihydrochloride | $10^{-3}$ mol | | |
| 2,3-diamino-6,7-dihydro-1H,5H-pyrazolo[1,2-a]pyrazol-1-one dimethanesulfonate | $10^{-3}$ mol | | |
| 2-[(3-aminopyrazolo[1,5-a]pyridin-2-yl]oxy]ethanol hydrochloride | $10^{-3}$ mol | | |
| 4-(3-aminopyrazolo[1,5-a]pyridin-2-yl)-1,1-dimethylpiperzin-1-ium chloride hydrochloride | | | $10^{-3}$ mol |
| Dye support (1) | () | () | (**) |
| Demineralized water qs | 100 g | 100 g | 100 g |
| Shade observed | Coppery red | Dark purple mahogany | bleu grey green |

(**): dye support (1) pH 9.5

| | |
|---|---|
| 96° ethyl alcohol | 20.8 g |
| 35% aqueous sodium metabisulfite solution | 0.23 g AM |
| Pentasodium salt of diethylenetriaminepentaacetic acid as an aqueous 40% solution | 0.48 g AM |
| C8-C10 alkyl polyglucoside as an aqueous 60% solution | 3.6 g AM |
| benzyl alcohol | 2.0 g |
| Polyethylene glycol containing 8 units of ethylene oxide | 3.0 g |
| $NH_4Cl$ | 4.32 g |
| Aqueous ammonia containing 20% $NH_3$ | 2.94 g |

At the time of use, each composition is mixed with an equal weight of 20-volumes oxygenated water (6% by weight). A final pH of 9.5 is obtained.

Each mixture obtained is applied to locks of grey hair containing 90% grey hairs. After a leave-in time of 30 minutes, the locks are rinsed, washed with a standard shampoo, rinsed again and then dried, to give the shades mentioned.

The invention claimed is:

1. A cationic meta-phenylenediamine compound of formula (I), acid addition salts thereof, and solvates thereof:

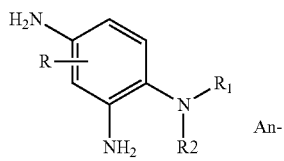

wherein:
R is chosen from a hydrogen or halogen atom; a $C_1$-$C_4$ alkyl group; a carboxyl group, or a $(C_1$-$C_4)$alkoxycarbonyl group;
R1 is chosen from a $C_1$-$C_{10}$ (hydroxy)alkyl group, optionally interrupted with one or more non-adjacent oxygen atoms or non-adjacent NR' substituents, substituted by a cationic CAT group;
R2 is chosen from a hydrogen atom or a $C_1$-$C_4$(hydroxy) alkyl group;
R1 and R2 may optionally form, together with the atom that bears them, a cationic heterocycle with 5 to 8 members;
R' is chosen from a hydrogen atom or a $C_1$-$C_4$(hydroxy) alkyl group; and
An- is chosen from an anion or a mixture of anions which are organic or inorganic and cosmetically acceptable.

2. The compound according to claim 1, wherein the cationic CAT group is chosen from straight or branched or heterocyclic groups comprising a quaternary ammonium of the type —$N^+$RaRbRc,
wherein Ra, Rb and Rc are independently chosen from a $C_1$-$C_6$ alkyl group which may optionally be substituted by a hydroxyl; and
Ra and Rb may optionally form a 5- to 10-membered heterocycle, in which case Rc is a $C_1$-$C_6$ alkyl group, optionally substituted by a hydroxyl group or a $C_1$-$C_4$ (hydroxy)alkyl group.

3. The compound according to claim 2, wherein Ra, Rb, Rc independently represent a $C_1$-$C_2$ alkyl group, optionally substituted by a hydroxyl group.

4. The compound according to claim 2, wherein the cationic CAT group is chosen from trimethylammonium, triethylammonium, dimethylethylammonium, diethylmethylammonium, diisopropylmethylammonium, hydroxyethyldiethylammonium, imidazolium, pyridinium, piperazinium, pyrrolidinium, morpholinium, pyrimidinium, thiazolium, benzimidazolium and piperidinium groups, or mixtures thereof.

5. The compound according to claim 1, wherein R represents a hydrogen atom.

6. The compound according to claim 1, wherein R2 represents a hydrogen atom or a $C_1$-$C_4$ alkyl group.

7. The compound according to claim 1, wherein R1 represents a $C_1$-$C_{10}$ alkyl group substituted by a cationic CAT group.

8. The compound according to claim 1, wherein R1 represents a $C_1$-$C_{10}$ alkyl group interrupted with an oxygen atom or an NR' substituent, substituted by a cationic CAT group.

9. The compound according to claim 7, wherein CAT designates a cationic group chosen from trimethylammonium, triethylammonium, dimethylethyl ammonium, diethylmethylammonium, diisopropylmethylammonium, diethylpropyl ammonium, hydroxyethyl diethyl ammonium, di-beta-hydroxyethylmethylammonium, tri-beta-hydroxyethylammonium groups, or mixtures thereof.

10. The compound according to claim 1, wherein CAT designates a 5- to 8-membered heterocyclic group of which one of the members is a quaternary ammonium, said heterocycle optionally substituted by one or more groups independently chosen from a hydroxyl group or a $C_1$-$C_4$ (hydroxy)alkyl group.

11. The compound according to claim 10, wherein CAT designates a pyrrolidine, piperidine, or piperazine group, optionally substituted by a cationic —$N^+$RaRbRc group, wherein Ra, Rb, Rc are independently chosen from a $C_1$-$C_6$ alkyl group, optionally substituted by a hydroxyl group.

12. The compound according to claim 11, wherein CAT designates a pyrrolidine or piperidine group, optionally substituted by a tri($C_1$-$C_4$)alkyl ammonium group.

13. The compound according to claim 1, wherein R1 and R2 form, together with the atom that bears them, a cationic 5- to 8-membered heterocycle.

14. The compound according to claim 13, wherein R1 and R2 form, together with the nitrogen atom that bears them, a 5- to 8-membered heterocyclic group of which one member is a quaternary ammonium, said heterocycle optionally substituted by one or more groups independently chosen from a hydroxyl group or a $C_1$-$C_4$ (hydroxy)alkyl group.

15. The compound according to claim 1, wherein R1 and R2 form, together with the nitrogen atom that bears them, a pyrrolidine or piperidine group, substituted by a cationic —N⁺RaRbRc group, wherein Ra, Rb, Rc are independently chosen from $C_1$-$C_6$ alkyl groups optionally substituted by a hydroxyl group, said cationic group being chosen from trimethylammonium, triethylammonium, dimethylethyl ammonium, or diethylmethylammonium groups.

16. The compound according to claim 1, chosen from:
2-[(2,4-diaminophenyl)amino]-N,N,N-trimethylethanaminium, An-,
3-[(2,4-diaminophenyl)amino]-N,N,N-trimethylpropan-1-aminium, An-,
4-{2-[(2-amino-5-hydroxyphenyl)amino]ethyl}-1,1-dimethylpiperazin-1-ium, An-,
4-{3-[(2,4-diaminophenyl)amino]propyl}-1,1-dimethylpiperazin-1-ium, An-,
4-{2-[(2,4-diaminophenyl)amino]ethyl}-1-(2-hydroxyethyl)-1-methylpiperazin-1-ium, An-,
1-{2-[(2,4-diaminophenyl)amino]ethyl}-1-methylpiperidinium, An-,
1-{3-[(2,4-diaminophenyl)amino]propyl}-1-methylpiperidinium, An-,
1-{2-[(2,4-diaminophenyl)amino]ethyl}-1-methylpyrrolidinium, An-,
1-{3-[(2,4-diaminophenyl)amino]propyl}-1-methylpyrrolidinium, An-,
4-{2-[(2,4-diaminophenyl)amino]ethyl}-4-methylmorpholin-4-ium, An-,
4-{3-[(2,4-diaminophenyl)amino]propyl}-4-methylmorpholin-4-ium, An-,
1-{2-[(2,4-diaminophenyl)amino]ethyl}-3-methyl-1H-imidazol-3-ium, An-,
1-{3-[(2,4-diaminophenyl)amino]propyl}-3-methyl-1H-imidazol-3-ium, An-,
2-[(2,4-diaminophenyl)(methyl)amino]-N,N,N-trimethylethanaminium, An-,
3-[(2,4-diaminophenyl)(methyl)amino]-N,N,N-trimethylpropan-1-aminium, An-,
1-{2-[(2,4-diaminophenyl)(methyl)amino]ethyl}-1-methylpyrrolidinium, An-,
1-{3-[(2,4-diaminophenyl)(methyl)amino]propyl}-1-methylpyrrolidinium, An-,
1-{2-[(2,4-diaminophenyl)(methyl)amino]ethyl}-1-methylpiperidinium, An-,
1-{3-[(2,4-diaminophenyl)(methyl)amino]propyl}-1-methylpiperidinium, An-,
4-{2-[(2,4-diaminophenyl)(methyl)amino]ethyl}-4-methylmorpholin-4-ium, An-,
4-{3-[(2,4-diaminophenyl)(methyl)amino]propyl}-4-methylmorpholin-4-ium, An-,
1-(2,4-diaminophenyl)-N,N,N-trimethylpyrrolidin-3-aminium, An-,
4-(2,4-diaminophenyl)-1,1-dimethylpiperazin-1-ium, An-,
4-(2,4-diaminophenyl)-1-(2-hydroxyethyl)-1-methylpiperazin-1-ium, An-,
4-(2,4-diaminophenyl)-1,1-bis(2-hydroxyethyl)piperazin-1-ium, An-,
1-(2,4-diaminophenyl)-N,N,N-trimethylpiperidin-4-aminium, An-,
1-[2-({2-[(2,4-diaminophenyl)amino]ethyl}amino) ethyl]-1-methylpiperidinium, An-,
1-[2-({2-[(2,4-diaminophenyl)amino]ethyl}amino) ethyl]-1-methylpyrrolidinium, An-,
1-[2-({2-[(2,4-diaminophenyl)amino]ethyl}amino) ethyl]-3-methyl-1H-imidazol-3-ium, An-,
4-[2-({2-[(2-amino-5-4-[2-({2-[(2,4-diaminophenyl) amino]ethyl}amino)ethyl]-4-methylmorpholin-4-ium, An-,
3-({2-[(2,4-diaminophenyl)amino]ethyl}amino)-N,N,N-trimethylpropan-1-aminium, An-,
2-{2-[(2,4-diaminophenyl)amino]ethoxy}-N,N,N-trimethylethanaminium, An-,
3-{2-[(2,4-diaminophenyl)amino]ethoxy}-N,N,N-trimethylpropan-1-aminium, An-,
1-(2-{2-[(2,4-diaminophenyl)amino]ethoxy}ethyl)-1-methylpiperidinium, An-,
1-(2-{2-[(2,4-diaminophenyl)amino]ethoxy}ethyl)-1-methylpyrrolidinium, An-,
4-(2-{2-[(2,4-diaminophenyl)amino]ethoxy}ethyl)-1,1-dimethylpiperazin-1-ium, An-,
4-(3-{2-[(2,4-diaminophenyl)amino]ethoxy}propyl)-1,1-dimethylpiperazin-1-ium, An-,
4-(2-{2-[(2,4-diaminophenyl)amino]ethoxy}ethyl)-4-methylmorpholin-4-ium, An-,
4-(3-{2-[(2,4-diaminophenyl)amino]ethoxy}propyl)-4-methylmorpholin-4-ium, An-,
1-(2-{2-[(2,4-diaminophenyl)amino]ethoxy}ethyl)-3-methyl-1H-imidazol-3-ium, An-,
1-(3-{2-[(2,4-diaminophenyl)amino]ethoxy}propyl)-3-methyl-1H-imidazol-3-ium, An-, and salts, solvates, isomers thereof, and mixtures thereof.

17. A composition for dyeing keratin fibers comprising, in a medium that is suitable for dyeing keratin fibers, at least one compound chosen from cationic meta-phenylenediamine compounds of formula (I), acid addition salts thereof, and solvates thereof:

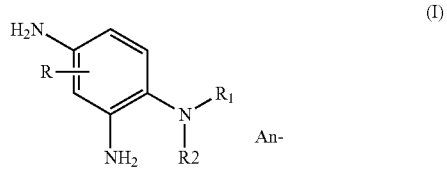

wherein:
R is chosen from a hydrogen or halogen atom; a $C_1$-$C_4$ alkyl group; a carboxyl group, or a ($C_1$-$C_4$)alkoxycarbonyl group;
R1 is chosen from a $C_1$-$C_{10}$ (hydroxy)alkyl group, optionally interrupted with one or more non-adjacent oxygen atoms or non-adjacent NR' substituents, substituted by a cationic CAT group;
R2 is chosen from a hydrogen atom or a $C_1$-$C_4$(hydroxy) alkyl group;
R1 and R2 may optionally form, together with the atom that bears them, a cationic heterocycle with 5 to 8 members;
R' is chosen from a hydrogen atom or a $C_1$-$C_4$(hydroxy) alkyl group; and
An- is chosen from an anion or a mixture of anions which are organic or inorganic and cosmetically acceptable.

18. A process for dyeing keratin fibers, comprising applying a dyeing composition to said fibers, either alone or in the presence of an oxidizing agent, for a time that is sufficient to develop the desired color, wherein said dyeing composition comprises at least one cationic meta-phenylenediamine compound of formula (I), acid addition salts thereof, and solvates thereof:

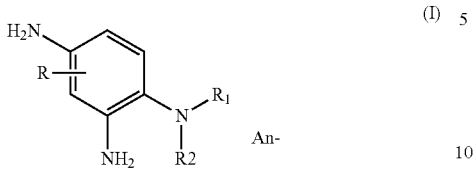

wherein:
- R is chosen from a hydrogen or halogen atom; a $C_1$-$C_4$ alkyl group; a carboxyl group, or a ($C_1$-$C_4$)alkoxycarbonyl group;
- R1 is chosen from a $C_1$-$C_{10}$ (hydroxy)alkyl group, optionally interrupted with one or more non-adjacent oxygen atoms or non-adjacent NR' substituents, substituted by a cationic CAT group;
- R2 is chosen from a hydrogen atom or a $C_1$-$C_4$(hydroxy)alkyl group;
- R1 and R2 may optionally form, together with the atom that bears them, a cationic heterocycle with 5 to 8 members;
- R' is chosen from a hydrogen atom or a $C_1$-$C_4$(hydroxy)alkyl group; and
- An- is chosen from an anion or a mixture of anions which are organic or inorganic and cosmetically acceptable.

* * * * *